(12) United States Patent  
Bonassar et al.

(10) Patent No.: US 9,242,031 B2  
(45) Date of Patent: *Jan. 26, 2016

(54) MODULAR FABRICATION SYSTEMS AND METHODS

(71) Applicant: Cornell Research Foundation, Inc., Ithaca, NY (US)

(72) Inventors: Lawrence Bonassar, Ithaca, NY (US); Hod Lipson, Ithaca, NY (US); Daniel L. Cohen, Ithaca, NY (US); Evan Malone, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/504,375

(22) Filed: Oct. 1, 2014

(65) Prior Publication Data

US 2015/0084238 A1    Mar. 26, 2015

Related U.S. Application Data

(63) Continuation of application No. 14/146,179, filed on Jan. 2, 2014, now Pat. No. 8,877,112, which is a continuation of application No. 13/052,787, filed on Mar. 21, 2011, now Pat. No. 8,636,938, which is a continuation of application No. 11/201,057, filed on Aug. 10, 2005, now Pat. No. 7,939,003.

(60) Provisional application No. 60/704,299, filed on Aug. 1, 2005, provisional application No. 60/600,529, filed on Aug. 11, 2004.

(51) Int. Cl.

| | |
|---|---|
| *B28B 1/14* | (2006.01) |
| *A61L 27/52* | (2006.01) |
| *B29C 67/00* | (2006.01) |
| *A61L 27/36* | (2006.01) |
| *A61L 27/38* | (2006.01) |
| *B33Y 10/00* | (2015.01) |

(Continued)

(52) U.S. Cl.  
CPC ............. *A61L 27/52* (2013.01); *A61L 27/36* (2013.01); *A61L 27/3817* (2013.01); *B29C 67/0055* (2013.01); *A61L 2430/10* (2013.01); *B33Y 10/00* (2014.12); *B33Y 50/02* (2014.12); *B33Y 70/00* (2014.12)

(58) Field of Classification Search  
USPC ................ 264/308; 438/1; 118/708; 101/491  
See application file for complete search history.

(56) References Cited

U.S. PATENT DOCUMENTS

| | | |
|---|---|---|
| 5,121,329 A | 6/1992 | Crump |
| 5,126,529 A | 6/1992 | Weiss et al. |

(Continued)

FOREIGN PATENT DOCUMENTS

WO    2005057436 A1    6/2005

OTHER PUBLICATIONS

Apr. 17, 2007, Office Action for U.S. Appl. No. 11/200,994.

(Continued)

*Primary Examiner* — Jacob Thomas Minskey  
(74) *Attorney, Agent, or Firm* — LeClairRyan, a Professional Corporation

(57) ABSTRACT

The present invention relates to an article fabrication system having a plurality of material deposition tools containing one or more materials useful in fabricating the article, and a material deposition device having a tool interface for receiving one of the material deposition tools. A system controller is operably connected to the material deposition device to control operation of the material deposition device. Also disclosed is a method of fabricating an article using the system of the invention and a method of fabricating a living three-dimensional structure.

19 Claims, 25 Drawing Sheets

(51) Int. Cl.
*B33Y 50/02* (2015.01)
*B33Y 70/00* (2015.01)

(56) References Cited

U.S. PATENT DOCUMENTS

| | | | |
|---|---|---|---|
| 5,134,569 A | 7/1992 | Masters | |
| 5,204,055 A | 4/1993 | Sachs et al. | |
| 5,260,009 A | 11/1993 | Penn | |
| 5,312,224 A | 5/1994 | Batchelder et al. | |
| 5,518,680 A | 5/1996 | Cima et al. | |
| 5,900,207 A | 5/1999 | Danforth et al. | |
| 6,030,199 A | 2/2000 | Tseng | |
| 6,036,777 A | 3/2000 | Sachs | |
| 6,153,034 A | 11/2000 | Lipsker | |
| 6,224,893 B1 | 5/2001 | Langer et al. | |
| 6,251,340 B1 | 6/2001 | Tseng | |
| 6,658,314 B1 | 12/2003 | Gothait | |
| 6,773,713 B2 | 8/2004 | Bonassar et al. | |
| 6,850,334 B1 | 2/2005 | Gothait | |
| 6,905,738 B2 | 6/2005 | Ringeisen et al. | |
| 6,986,739 B2 | 1/2006 | Warren et al. | |
| 7,168,935 B1 | 1/2007 | Taminger et al. | |
| 7,195,475 B2 | 3/2007 | Silverbrook | |
| 7,220,112 B2 | 5/2007 | Silverbrook | |
| 7,220,115 B2 | 5/2007 | Silverbrook | |
| 7,306,323 B2 | 12/2007 | Silverbrook | |
| 7,322,674 B2 | 1/2008 | Silverbrook | |
| 2002/0149137 A1 | 10/2002 | Jang et al. | |
| 2002/0159982 A1 | 10/2002 | Bonassar et al. | |
| 2002/0182241 A1 | 12/2002 | Borenstein et al. | |
| 2003/0170285 A1 | 9/2003 | Veazey et al. | |
| 2004/0094058 A1 | 5/2004 | Kasperchik et al. | |
| 2004/0143358 A1 | 7/2004 | Silverbrook | |
| 2004/0237822 A1 | 12/2004 | Boland et al. | |
| 2005/0253308 A1 | 11/2005 | Sherwood | |
| 2006/0156978 A1 | 7/2006 | Bonassar et al. | |
| 2006/0160250 A1 | 7/2006 | Bonassar et al. | |
| 2007/0182799 A1 | 8/2007 | Silverbrook | |
| 2008/0001997 A1 | 1/2008 | Silverbrook | |
| 2008/0062214 A1 | 3/2008 | Silverbrook | |
| 2008/0068416 A1 | 3/2008 | Silverbrook | |
| 2008/0084450 A1 | 4/2008 | Silverbrook | |

OTHER PUBLICATIONS

Oct. 31, 2007, Office Action for U.S. Appl. No. 11/200,994.
Apr. 24, 2008, Office Action for U.S. Appl. No. 11/200,994.
Sep. 9, 2008, Office Action for U.S. Appl. No. 11/200,994.
Feb. 9, 2009, Office Action for U.S. Appl. No. 11/200,994.
Aug. 21, 2009, Notice of Allowance for U.S. Appl. No. 11/200,994.
Chang et al., "Injection Molding of Chondrocyte/Alginate Constructs in the Shape of Facial Implants," J. Biomed. Mat. Res. 55:503-411 (2001).
Cohen et al., "Direct Freeform Fabricaiton of Spatially Heterogeneous Living Pre-Cell-Seeded Implants," Proceedings of the 15th Solid Freeform Fabrication Symposium, Austin, Texas (2004).
Czaplewski et al., "Nanofluidic Channels with Elliptical Cross Sections Formed using a Nonlithographic Process," App. Phys. Lett. 83(23):4836-4838 (2003).
Czaplewski et al., "Nonlithographic Approach to Nanostructure Fabrication using a Scanned Electrospinning Source," J. Vac. Sci. Tchnol. B 21(6):2994-2997 (2003).
Fuller et al., "Ink-jet Printed Nanoparticle Microelectromechanical Systems," J. Microelectromech. Sys. 11:54-60 (2002).
Genes et al., "Effect of Substrate Mechanics on Chondrocyte Adhesion to Modified Alginate Surfaces," Arch. Biochem. Biophys. 422:161-167 (2004).
Hung et al., "Anatomically Shaped Osteochondral Constructs for Articular Cartilage Repair," J. Biomech. 36:1853-1864 (2003).
Kameoka & Craighead, "Fabrication of Oriented Polymeric Nanofibers on Planar Surfaces by Electrospinning," Applied Physics Letters 83(2):371-373 (2003).
Kameoka et al., "A Scanning Tip Electrospinning Source for Deposition of Oriented Nanofibres," Nanotechnology 14:1124-1129 (2003).
Kameoka et al., "Fabrication of Suspended Silica Glass Nanofibers from Polymeric Materials Using a Scanned Electrospinning Source," Nano Letters 4(11):2105-2108 (2004).
Kameoka et al., "Polymeric Nanowire Architecture," J. Mater. Chem. 14:1503-1505 (2004).
Kim et al., "Experimental Model for Cartilage Tissue Engineering to Regenerate the Zonal Organization of Articular Cartilage," Osteoarthritis Cartilage 00:1-12 (2003).
Klein et al., "Tissue Engineering of Stratified Articular Cartilage from Chondrocyte Subpopulations," Osteoarthritis Cartilage 11:595-602 (2003).
Landers et al., "Desktop Manufacturing of Complex Objects, Prototypes and Biomedical Scaffolds by Means of Computer-Assisted Design Combined with Computer-guided 3D Plotting of Polymers and Reactive Oligomers," Macromol. Mater. Eng. 282:17-21 (2000).
Lipson & Bongard, "An Exploration-Estimation Algorithm for Synthesis and Analysis of Engineering Systems Using Minimal Physical Testing," Proceedings of the ASME Design Automation Conference (DAC04), Salt Lake City, UT (2004).
Malone & Lipson, "Freeform Fabrication of Electroactive Polymer Actuators and Electromechanical Devices," Proceedings of the 15th Solid Freeform Fabrication Symposium, Austin, TX (2004).
Malone & Lipson, "Functional Freeform Fabrication for Physical Artificial Life," Proceedings of the 9th International Conference on Artificial Life (ALIFE IX) (2004).
Malone & Lipson, "Solid Freeform Fabrication for Autonomous Manufacturing of Complete Mobile Robots," Proceedings of Robosphere 2004, NASA Ames Research Center, CA, USA (2004).
Malone & Lipson, "Solid Free-Form Fabrication for Self-Sustained Robot Ecologies: Challenges and Opportunities," Proceedings of Robosphere 2002, NASA Ames Research Center, CA, USA (2002).
Malone & Purwin, "Application of Machine Learning Methods to the Open-Loop Control of a Freeform Fabrication System," Proceedings of the 15th Solid Freeform Fabrication Symposium, Austin, TX (2004).
Malone et al., "Freeform Fabrication of Zinc-Air Batteries and Electromechanical Assemblies," Rapid Prototyping Journal 10(1):58-69 (2004).
Malone et al., "Freeform Fabrication of Zinc-Air Batteries and Electromechanical Assemblies," Proceedings of the 14th Solid Freeform Fabrication Symposium, Austin, TX, (2003).
Mironov et al., "Organ Printing: Computer-Aided Jet-based 3D Tissue Engineering," Trends in Biotechnology 21 (4):157-161 (2003).
Ouyang et al., "Rapid Prototyping and Characterization of a WC-(NiSiB Alloy) Cermet/Tool Steel Functionally Graded Material (FGM) Synthesized by Laser Cladding," in Rapid Prototyping of Materials, F.D.S. Marquis and D.L. Bourell Eds., TMS (The Minerals, Metals & Materials Society) 77-93 (2002).
Pfister et al., "Biofunctional Rapid Prototyping for Tissue-Engineering Applications: 3D Bioplotting Versus 3D Printing," Journal of Polymer Science Part A: Polymer Chemistry 42:624-638 (2004).
Roth et al., "Inkjet Printing for High-Throughput Cell Patterning," Biomaterials 25:3707-3715 (2004).
Smurov et al., "Laser-assisted Direct Manufacturing of Functionally Graded 3D Objects by Coaxial Powder Injection," Proceedings of the SPIE—The International Society for Optical Engineering 5399:27-37 (2004).
Sun et al., "Multi-nozzle Biopolymer Deposition for Tissue Engineering Application," 6th International Conference on Tissue Engineering, Orlando, FL (Oct. 10-13, 2003) (Abstract only).
Xu et al., "Injectable Tissue-Engineered Cartilage with Different Chondrocyte Sources," Plast. Reconstr. Surg. 113(5):1361-1371 (2004).

FIG. 20A 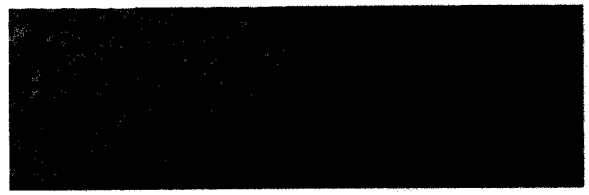 FIG. 20B
FIG. 21A   FIG. 21B

FIG. 24A 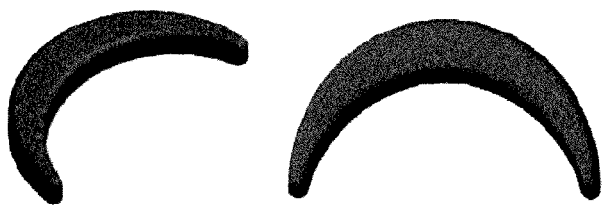 FIG. 24B
FIG. 24C 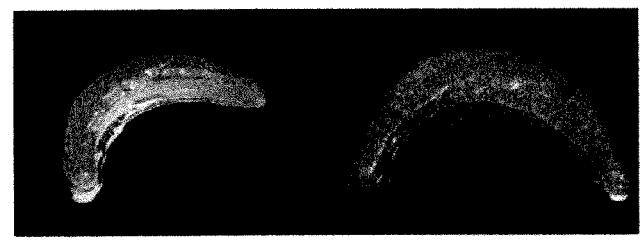 FIG. 24D
FIG. 24E 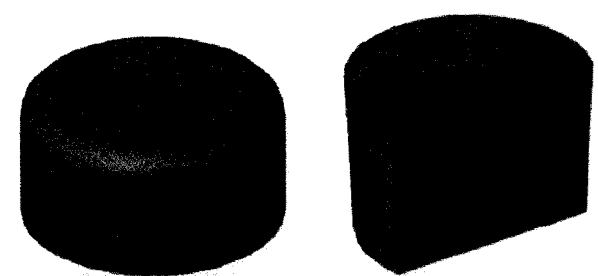 FIG. 24F
FIG. 24G  FIG. 24H
FIG. 24I 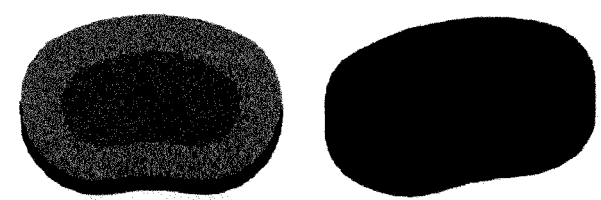 FIG. 24J
FIG. 24K 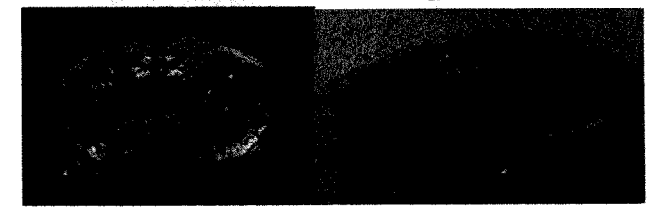 FIG. 24L

US 9,242,031 B2

MODULAR FABRICATION SYSTEMS AND METHODS

This application is a continuation of U.S. patent application Ser. No. 14/146,179, filed Jan. 2, 2014, which is a continuation of U.S. patent application Ser. No. 13/052,787, filed Mar. 21, 2011, now U.S. Pat. No. 8,636,938, which is a continuation of U.S. patent application Ser. No. 11/201,057, filed Aug. 10, 2005, now U.S. Pat. No. 7,939,003, which claims the priority benefit of U.S. Provisional Patent Application Ser. No. 60/704,299, filed Aug. 1, 2005, and U.S. Provisional Patent Application Ser. No. 60/600,529, filed Aug. 11, 2004, all of which are hereby incorporated by reference in their entirety.

FIELD OF THE INVENTION

The present invention relates generally to an article fabrication system, a method of fabricating an article, and a method of fabricating a living three-dimensional structure.

BACKGROUND OF THE INVENTION

Solid freeform fabrication ("SFF") is the name given to a class of manufacturing methods which allow the fabrication of three-dimensional structures directly from computer-aided design ("CAD") data. SFF processes are generally additive, in that material is selectively deposited to construct the product rather than removed from a block or billet. Most SFF processes are also layered, meaning that a geometrical description of the product to be produced is cut by a set of parallel surfaces (planar or curved), and the intersections of the product and each surface—referred to as slices or layers—are fabricated sequentially. Together, these two properties mean that SFF processes are subject to very different constraints than traditional material removal-based manufacturing. Nearly arbitrary product geometries are achievable, no tooling is required, mating parts and fully assembled mechanisms can be fabricated in a single step, and multiple materials can be combined, allowing functionally graded material properties. New features, parts, and even assembled components can be "grown" directly on already completed objects, suggesting the possibility of using SFF for the repair and physical adaptation of existing products. On the other hand, a deposition process must be developed and tuned for each material, geometry is limited by the ability of the deposited material to support itself and by the (often poor) resolution and accuracy of the process, and multiple material and process interactions must be understood.

SFF has traditionally focused on printing passive mechanical parts or products in a single material, and the emphasis of research has been on developing new deposition processes (U.S. Pat. No. 5,121,329 to Crump; U.S. Pat. No. 5,134,569 to Masters; U.S. Pat. No. 5,204,055 to Sachs et. al.; and U.S. Pat. No. 5,126,529 to Weiss et. al.), on improving the quality, resolution, and surface finish of fabricated products, and on broadening the range of single materials which can be employed by a given SFF process, including biocompatible polymers and other biomaterials (Pfister et al., "Biofunctional Rapid Prototyping for Tissue-engineering Applications: 3D Bioplotting Versus 3D Printing," *Journal of Polymer Science Part A: Polymer Chemistry* 42:624-638 (2004); Landers et al., "Desktop Manufacturing of Complex Objects, Prototypes and Biomedical Scaffolds by Means of Computer-assisted Design Combined with Computer-guided 3D Plotting of Polymers and Reactive Oligomers," *Macromolecular Materials and Engineering* 282:17-21 (2000)), and living cells (Roth et al., "Inkjet Printing for High-throughput Cell Patterning," *Biomaterials* 25:3707-3715 (2004)). These improvements have allowed freeform fabrication to become a viable means of manufacturing finished functional parts, rather than only prototypes.

More recently, the greater utility of freeform fabricated products having multiple materials has been recognized, prompting reexamination and novel research into processes which can fabricate using multiple materials (U.S. Pat. No. 5,260,009 to Penn), and which can thereby produce complex articles with a variety of functionality, including functionally graded materials (Ouyang et al., "Rapid Prototyping and Characterization of a WC-(NiSiB Alloy) Ceramet/Tool Steel Functionally Graded Material (FGM) Synthesized by Laser Cladding," Columbus, Ohio, USA: TMS—Miner. Metals & Mater. Soc. (2002); Smurov et al., "Laser-assisted Direct Manufacturing of Functionally Graded 3D Objects by Coaxial Powder Injection," *Proceedings of the SPIE—The International Society for Optical Engineering* 5399:27 (2004)), electronics, MEMS (Fuller et al., "Ink jet Printed Nanoparticle Microelectromechanical Systems," *Journal of Microelectromechanical Systems* 11:54-60 (2002)), living tissue constructs (Mironov et al., "Organ Printing: Computer-aided Jet-based 3D Tissue Engineering," *Trends in Biotechnology* 21:157-161 (2003)), and compositions of living and nonliving materials (Sun et al., "Multinozzle Biopolymer Deposition for Tissue Engineering Application," *6th International Conference on Tissue Engineering*, Orlando, Fla. (Oct. 10-13, 2003); International Patent Application No. PCT/US2004/015316 to Sun et al.; and U.S. Pat. No. 6,905,738 to Ringeisen et al.). All of these systems still depend upon a small fixed set of deposition process technologies, and are therefore limited to the materials which can be adapted to those processes, by the effects of those particular processes on the materials, and by the fabrication rates and resolutions of those processes. In particular, the system of U.S. Pat. No. 6,905,738 to Ringeisen et al., requires that for every material to be deposited, a two material system be developed comprising the material to be transferred, and a compatible matrix material which is vaporized by the laser in order to propel the transfer material to the substrate. In addition, this system has only demonstrated fabrication of thin films of materials—its ability to deposit many layers of materials is not well established. The system and method of Sun et al., "Multinozzle Biopolymer Deposition for Tissue Engineering Application," *6th International Conference on Tissue Engineering*, Orlando, Fla. (Oct. 10-13, 2003) and International Patent Application No. PCT/US2004/015316 to Sun et al., is limited to a fixed set of four deposition processes and requires that the alginate materials be deposited into a bath of liquid crosslinking agent—a limitation it shares with the work of Pfister et al., "Biofunctional Rapid Prototyping for Tissue-engineering Applications: 3D Bioplotting Versus 3D Printing," *Journal of Polymer Science Part A: Polymer Chemistry* 42:624-638 (2004) and Landers et al., "Desktop Manufacturing of Complex Objects, Prototypes and Biomedical Scaffolds by Means of Computer-assisted Design Combined with Computer-guided 3D Plotting of Polymers and Reactive Oligomers," *Macromolecular Materials and Engineering* 282:17-21 (2000). In addition, none of these systems explicitly measures the properties of, and monitors and controls the conditions experienced by the fabrication materials, the fabrication substrate, and the article under construction before, during, and/or after fabrication as an intrinsic part of the fabrication process and manufacturing plan. The fabrication process is thus limited to the spatial control of material placement on relatively simple, passive substrates. Temporal control of the evolution of material properties is therefore not possible, and complex substrates whose state must be controlled and monitored continuously are not readily accommodated. Fabricating into or onto substrates, such as living organisms or devices which must remain in operation continuously, is problematic.

A major challenge in orthopaedic tissue engineering is the generation of seeded implants with structures that mimic native tissue, both in terms of anatomic geometries and intratissue cell distributions. Previous studies have demonstrated that techniques such as injection molding (Chang et al., "Injection Molding of Chondrocyte/Alginate Constructs in the Shape of Facial Implants," *J. Biomed. Mat. Res.* 55:503-511 (2001)) and casting (Hung et al., "Anatomically Shaped Osteochondral Constructs for Articular Cartilage Repair," *J. Biomech.* 36:1853-1864 (2003)) of hydrogels can generate cartilage tissue in complex geometries. Other studies have investigated methods to reproduce regional variations in articular cartilage constructs by depositing multiple layers of chondrocytes (Klein et al., "Tissue Engineering of Stratified Articular Cartilage from Chondrocyte Subpopulations," *Osteoarthritis Cartilage* 11:595-602 (2003)) or chondrocyte-seeded gels (Kim et al., "Experimental Model for Cartilage Tissue Engineering to Regenerate the Zonal Organization of Articular Cartilage," *Osteoarthritis Cartilage* 11:653-664 (2003)). However, there remains no viable strategy for rapidly producing implants with correct anatomic geometries and cell distributions. Recently, advances in SFF techniques have enabled the deposition of multilayered structures composed of multiple chemically active materials (Malone et al., "Freeform Fabrication of 3D Zinc-Air Batteries and Functional Electro-Mechanical Assemblies," *Rapid Prototyping Journal* 10:58-69 (2004)). Applicants believe that this technology has the potential to be adapted to the fabrication of living tissue under conditions that preserve cell viability.

The present invention is directed at overcoming disadvantages of prior art approaches and satisfying the need to establish a robust and reliable SFF system and method.

SUMMARY OF THE INVENTION

One aspect of the present invention relates to an article fabrication system. The system has a plurality of material deposition tools containing one or more materials useful in fabricating the article. The system has a material deposition device having a tool interface for receiving the material deposition tools, the tool interface of the material deposition device being movable relative to a substrate to dispense material from the material deposition tool to the substrate. A system controller is operably connected to the material deposition device to control operation of the material deposition device.

Another aspect of the present invention relates to a method of fabricating an article. This method involves providing the above-described article fabrication system. Material is dispensed from the material deposition tools, when mounted on the tool interface of the material deposition device, in amounts and at positions on the substrate in response to instructions from the system controller, whereby an article is fabricated on the substrate.

A further aspect of the present invention relates to a method of fabricating a living three-dimensional structure. This method involves providing a data set representing a living three-dimensional structure to be fabricated. One or more compositions including a composition having a hydrogel with seeded cells is provided. The one or more compositions are dispensed in a pattern in accordance with the data set suitable to fabricate the living three-dimensional structure.

Yet another aspect of the present invention relates to an article fabrication system. The system has a material deposition tool containing one or more materials useful in fabricating the article. The system has a material deposition device having a tool interface for receiving the material deposition tool, the tool interface of the material deposition device being movable relative to a substrate to dispense material from the material deposition tool to the substrate. The system has an enclosure defining a receptacle for enclosing the substrate in a confined environment segregated from other components of the system and capable of receiving material dispensed from the material deposition tool. A system controller is operably connected to the material deposition device to control operation of the material deposition device.

Yet a further aspect of the present invention relates to an article fabrication system. The system has a material deposition tool containing one or more materials useful in fabricating the article. The system has a material deposition device having a tool interface for receiving said material deposition tool, the tool interface of the material deposition device being movable relative to a substrate to dispense material from the material deposition tool to the substrate. The system has one or more sensors positioned to detect non-geometric properties of material dispensed to the substrate. A system controller is operably connected to the sensors to control detection of material properties and to the material deposition device to control the material deposition device.

The present invention relates to an article fabrication system having multiple interchangeable material deposition tools and one or more modules capable of receiving material dispensed from material deposition tools. The deposition tools may contain interchangeable cartridges containing materials useful in fabricating the article. The tools and/or the cartridges may also contain apparatus for monitoring and conditioning the material for deposition. The substrate modules are useful in fabricating the article, and may also contain apparatus for monitoring and conditioning the deposited materials.

The system may also have a device to automatically switch tools and their cartridges and substrate modules, or these may be fixed in the system. A system controller is operably connected to the material tools, cartridges, substrate modules, transfer devices, and positioning systems. The system has provision for monitoring and controlling the environmental conditions under which fabrication takes place, for monitoring and correcting fabrication errors during the course of fabrication, and for monitoring and controlling the properties of the article being fabricated during the course of fabrication. The combined capabilities of the system, the deposition tools, and the substrate modules allow monitoring and control of the conditions experienced by all of the materials and by the article being fabricated, before, during, and/or after the fabrication process. This extends the freeform fabrication process to include controlled evolution of material properties as well as controlled deposition of multiple materials, allowing not just geometric, but spatio-temporal control over the properties of the composite article being fabricated. These extended capabilities are especially important when fabricating integrated systems comprising multiple active materials, such as electrochemical devices and living tissue constructs. This is also the case when depositing constructs into sensitive substrates, such as living organisms or sensing devices, the health and function of which must be maintained throughout the fabrication process.

The present invention's modular system architecture and multi-level control scheme give it distinct advantages over other systems. The modular system architecture enables the system of the present invention to adapt to high throughput applications, in which material changes and substrate changes must be efficient and, in some cases, in which automation would be beneficial. The modular design also enables the system to adapt to a broad range of applications. For example, the same general system design could be used for in vitro as well as in vivo fabrication.

The multi-level sensing, actuation, control, and intelligence enables the system to log and/or control the spatio-temporal state of numerous properties of both materials and articles being fabricated prior, during, and after fabrication (for example, from the start of the fabrication process through incubation). These material and article properties include but are not limited to temperature, humidity, light, vibration, pressure, mechanical loading, and shape. Spatio-temporal control of numerous properties is important when fabricating integrated systems with active materials such as electromechanical devices, self-assembling structures, and living tissue constructs.

BRIEF DESCRIPTION OF THE DRAWINGS

FIGS. 8A-B illustrate perspective, exploded views of the parts of a syringe which fit into the syringe cartridge. FIG. 8C illustrates a perspective, exploded view of how the syringe fits into the syringe cartridge. FIG. 8D illustrates a perspective view of the cartridge holding tool fitted with the syringe cartridge.

FIGS. 20A-B are photographs showing the results of viability tests in which both live (FIG. 20A) and dead (FIG. 20B) cells were detected in printed gels.

FIG. 21A is a stereolithography ("STL") image of a bovine meniscus generated by a CT scan. FIG. 21B is a photograph of the printed meniscus-shaped gel using the fabrication system and method of the present invention.

FIGS. 24A-L are photographs of printed gels using the fabrication system method of the present invention compared to images generated by CT scans.

DETAILED DESCRIPTION OF THE INVENTION

One aspect of the present invention relates to an article fabrication system. The system has a plurality of material deposition tools containing one or more materials useful in fabricating the article. The system has a material deposition device having a tool interface for receiving the material deposition tools, the tool interface of the material deposition device being movable relative to a substrate to dispense material from the material deposition tool to the substrate. A system controller is operably connected to the material deposition device to control operation of the material deposition device.

Another aspect of the present invention relates to an article fabrication system. The system has a material deposition tool containing one or more materials useful in fabricating the article. The system has a material deposition device having a tool interface for receiving the material deposition tool, the tool interface of the material deposition device being movable relative to a substrate to dispense material from the material deposition tool to the substrate. The system has an enclosure defining a receptacle for enclosing the substrate in a confined environment segregated from other components of the system and capable of receiving material dispensed from the material deposition tool. A system controller is operably connected to the material deposition device to control operation of the material deposition device.

A further aspect of the present invention relates to an article fabrication system. The system has a material deposition tool containing one or more materials useful in fabricating the article. The system has a material deposition device having a tool interface for receiving said material deposition tool, the tool interface of the material deposition device being movable relative to a substrate to dispense material from the material deposition tool to the substrate. The system has one or more sensors positioned to detect non-geometric properties of material dispensed to the substrate. A system controller is operably connected to the sensors to control detection of material properties and to the material deposition device to control the material deposition device.

Figure 1:
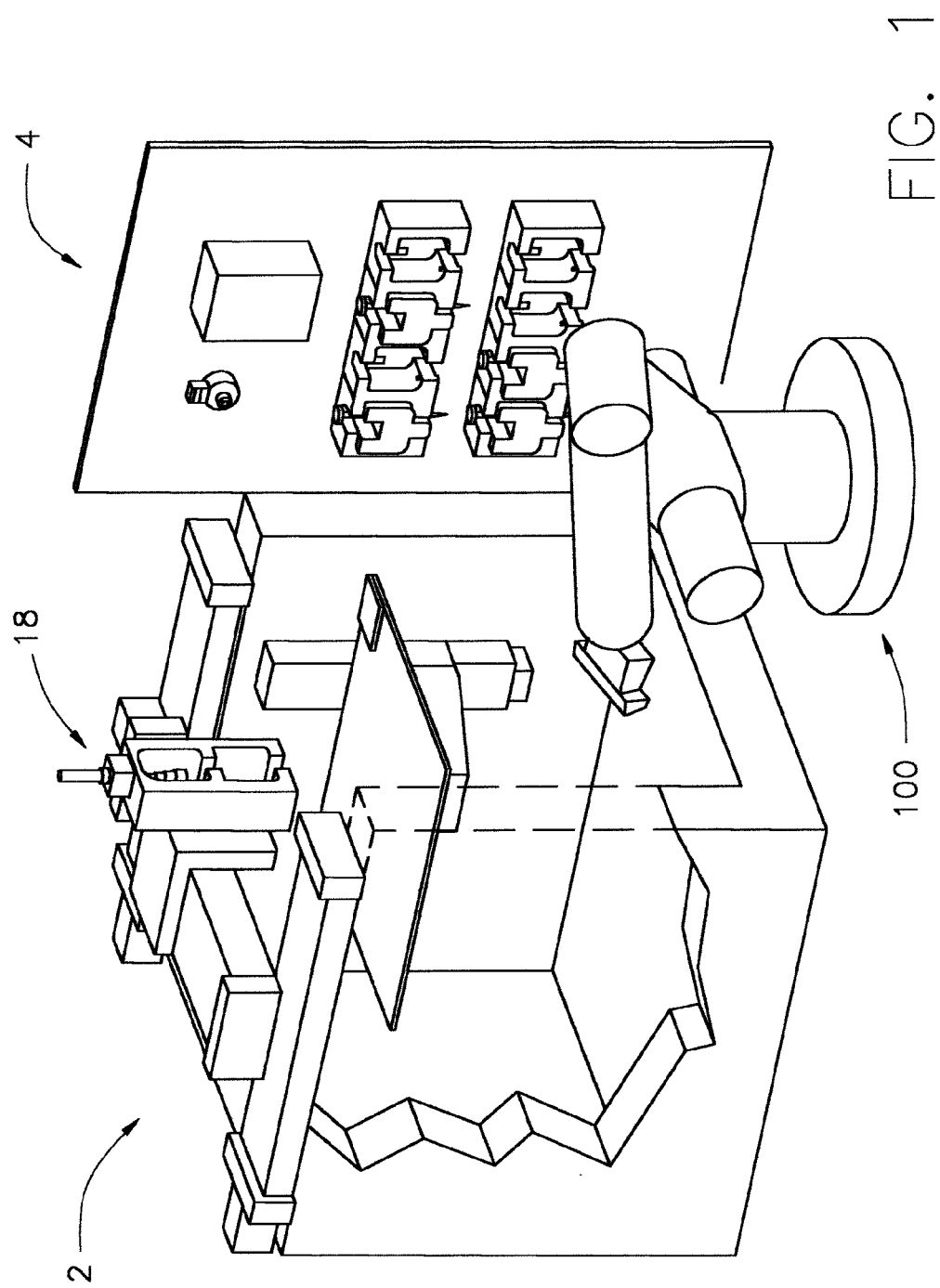
FIG. 1 is a perspective view of a fabrication system in accordance with the present invention.

FIG. 1 is a perspective view of one embodiment of the system of the present invention. In the particular embodiment shown in FIG. 1, tool rack 4 is connected to material deposition device 2. Located near material deposition device 2 and tool rack 4 is transfer device 100, which is capable of making contact with material deposition tool 18 and moving material deposition tools 18 between material deposition device 2 and tool rack 4.

Figure 2:
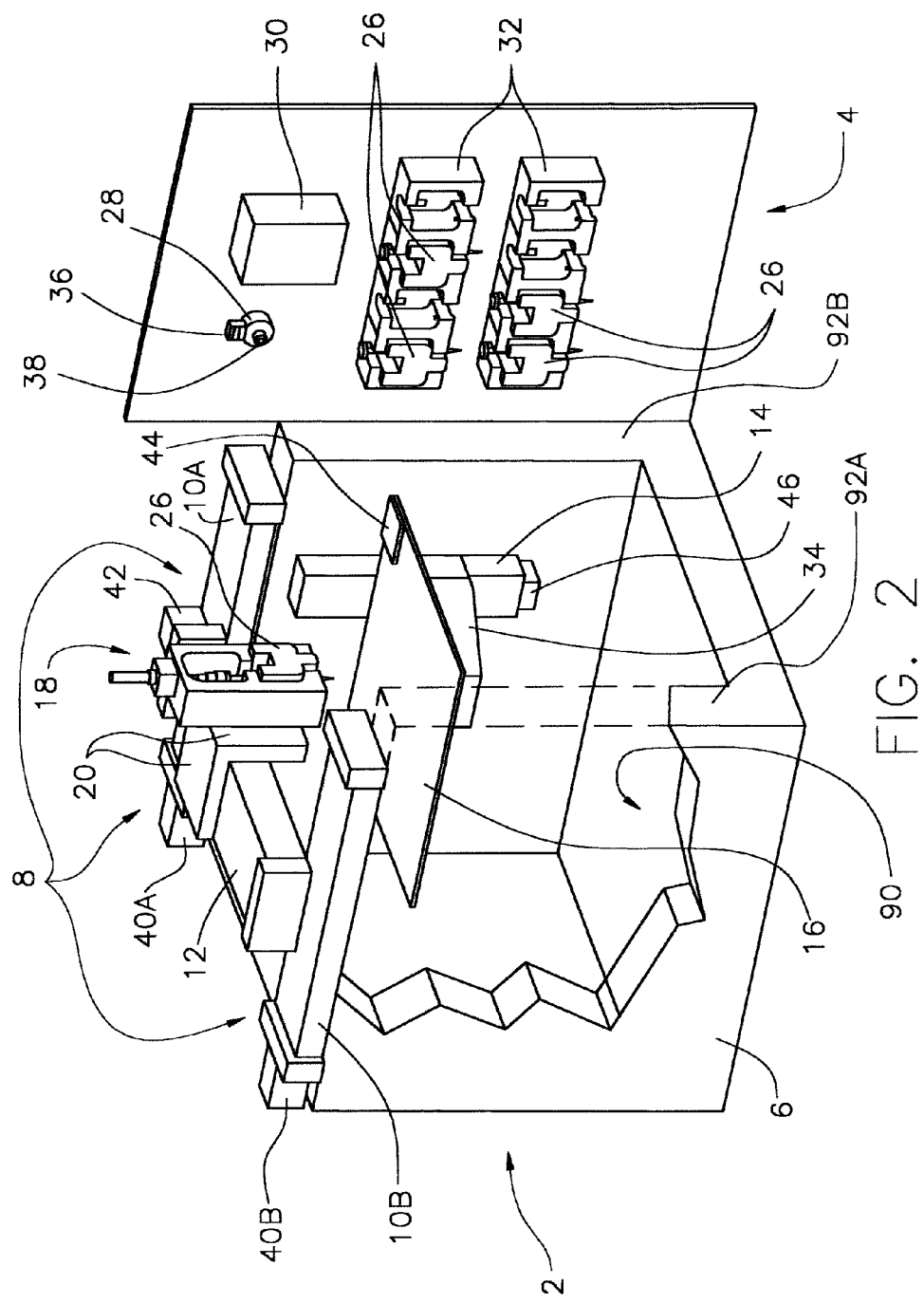
FIG. 2 is a perspective view of a material deposition device and the tool rack of the system in accordance with the present invention in which the tool rack is connected to the material deposition device.

Material deposition device 2 and tool rack 4 are again illustrated in perspective in FIG. 2. As shown, machine base 6 is the general supporting structure of material deposition device 2. Machine base 6 preferably has horizontal surface 90 which may rest on the ground or on a flat surface, such as the top of a bench or a table, and two vertical surfaces 92A-B connected to horizontal surface 90. In a preferred embodiment, machine base 6 is a large, precision granite structure, although other materials may be used in the construction of machine base 6 so long as the material is capable of dissipating vibration from the high acceleration motions that material deposition device 2 is capable of.

Positioning system 8 is preferably a machine driven X-Y coordinate gantry supported by machine base 6. Positioning system 8 has two X-axis stages, including first X-axis stage 10A and second X-axis stage 10B, preferably constructed of commercially available ballscrew stages. X-axis stages 10A-B rest on, and are attached to, vertical walls 92A-B of machine base 6. Positioning system 8 is preferably constructed of a commercially available ballscrew stage identical to X-axis stages 10A-B. Y-axis stage 12 is fixed, at opposite ends and perpendicular to, first X-axis stage 10A and second X-axis stage 10B and spans horizontal surface 90.

Movement at positioning system 8 occurs as Y-axis stage 12 moves back and forth along X-axis stages 10A-B. This movement is driven by motors 40A-B which, in a preferred embodiment, are high-performance brushless DC motors with optical encoders for displacement feedback. However, any motor which is capable of producing relatively high acceleration, good velocity regulation, and positioning accuracy may be used to operate the movement of positioning system 8. In operation, motor 40A drives one end of Y-axis stage 12 along X-axis stage 10A while motor 40B simultaneously drives the other end of y-axis stage 12 along X-axis stage 10B.

Another moving component of positioning system 8 is tool interface 20, which resides on Y-axis stage 12 and moves back and forth along Y-axis stage 12. Tool interface 20 is capable of receiving a material deposition tool, such as material deposition tool 18 illustrated in FIG. 2. As discussed in greater detail below, material deposition tool 18 may receive material cartridges, such as material cartridge 26. Movement of tool interface 20 along Y-axis stage 12 is driven by motor 42, which is preferably a motor similar to, or identical to, motors 40A-B. With tool interface 20 being capable of moving back and forth along Y-axis stage 12 and Y-axis stage 12 being capable of moving back and forth along X-axis stages 10A-B, positioning system 8 is capable of moving tool interface 20 in virtually any direction on a horizontal plane above horizontal surface 90.

Above horizontal surface 90 of machine base 6 and below positioning system 8 is substrate 16. Substrate 16 is a build surface upon which material from material deposition tool 18 is deposited. In a preferred embodiment, substrate 16 is equipped with calibration device 44, which may be fixed anywhere on substrate 16, but is preferably fixed to an outer edge or corner of substrate 16. Calibration device 44 is described in greater detail below. Substrate 16 is preferably constructed of a precision-ground aluminum plate, but may be constructed of any material capable of ensuring planarity. Substrate 16 rests on support structure 34, which holds substrate 16 in a horizontal position or, alternatively, may be adjusted to change the orientation (i.e., angle) of the surface plane of substrate 16 relative to positioning system 8. Support structure 34 is preferably of rigid construction.

In the particular embodiment illustrated in FIG. 2, support structure 34 is connected to Z-axis stage 14. Z-axis stage 14 is preferably a commercially available ballscrew stage, identical to X-axis stages 10A-B and Y-axis stage 12. Support structure 34 moves along Z-axis stage 14 in a vertical direction either towards or away from positioning system 8, thereby adjusting the vertical distance of substrate 16 relative to the material deposition tool (e.g., material deposition tool 18) connected to tool interface 20 of positioning system 8.

In operation, material deposition device 2 fabricates a product as positioning system 8 moves material deposition tool 18 in a pathway along substrate 16 and material deposition tool 18 deposits material onto substrate 16 along the pathway. Typically, fabrication of a product is carried out by layer-wise deposition of the material. This standard planar layered deposition approach to material deposition device 2 enables the system to deposit materials from material deposition tool 18 in a manner which optimizes the properties of the deposited material relative to the specified performance metrics for the product being fabricated—including alignment of deposited material fibers along primary stress axes to improve mechanical performance, depositing polymer materials in a manner which increases the degree of molecular alignment, and improving e.g., electrical or mechanical properties.

Alternative embodiments of material deposition device 2 may be designed to permit a less massive machine base to be used. For example, a cable and pulley arrangement could be used to create a Cartesian gantry robot in which the motors remain stationary (mounted on the machine base), thereby reducing the moving mass of the system and the reaction forces. This in turn would allow the use of a smaller, lighter machine base without compromising stability and precision. Alternative embodiments may make use of other means of moving the positioning system components, including linear electromagnetic motors, pneumatics, or hydraulics.

Alternative embodiments of material deposition device 2 can also make use of other positioning systems including, but not limited to, articulated robotic arms for the positioning and traversing of the material deposition tools and/or the positioning of the substrate. This would permit the material deposition device to make use of non-planar deposition paths (3-D curves) and more complex manipulation of objects being fabricated. This would also provide more freedom for the manufacturing planning components of the system to arrive at plans which more closely match the specifications of the desired product, which may include the ability to achieve 3-D curvilinear optimization of fiber or molecular alignment in deposited materials.

Further illustrated in FIG. 2 is tool rack 4 which, in the particular embodiment shown, is connected to material deposition device 2. In an alternative embodiment, tool rack 4 may be located in proximity to material deposition device 2 rather than being connected. Tool rack 4 is equipped with tool mounts, such as tool mount 28, which are capable of receiving a variety of material deposition tools, represented by mounted tool 30 and described in further detail below. A preferred tool mount of tool rack 4 is illustrated as tool mount 28, which has fluid/gas and electrical connectors 36 and mechanical connectors 38. Fluid/gas and electrical connectors 36 and mechanical connectors 38 allow tool rack 4 to be in electrical, fluid/gas, and/or mechanical communication with tools stored on tool rack 4. Tool rack 4 may also be equipped with cartridge holding devices 32 that are capable of receiving individual material cartridges 26. Tool rack 4 may also be equipped with substrate module holding devices that are capable of receiving individual or groupings of substrate modules. Substrate module holding devices may include electronic, mechanical, and/or auxiliary material interfaces which permit communication between any embedded intelligence and control in the substrate modules and the tool rack and hence the system controller. These interfaces may also provide utilities and auxiliary materials which may be used for the monitoring and control of the state of the substrate module and its contents.

In a preferred embodiment, tool rack 4 is designed to provide utility services to material deposition tools and material cartridges which are stored on it, and to provide communication between the material deposition tools and the system controller. Particular services include, without limitation, power, data communication, commands, fluids, and compressed gas. Data communication can take place between the material deposition tools and material cartridges stored on tool rack 4 and the system controller to enable the real-time status of materials and material deposition tools to be controlled and/or monitored while they are not in use. Data communication further allows the status to be used during manufacturing planning and allows the inventory to be managed. For example, requests for additional material can be made to a user if the system finds that tool rack 4 does not contain sufficient quantity of a material required in the current manufacturing task. The data communication also allows the system controller and/or user to reprogram, query, monitor, and/or control any embedded intelligence, sensors, and/or actuators in the material deposition tools or material cartridges. This can include updating the identity and/or status of materials contained in a tool or cartridge, and updating the internal control parameters of a material cartridge and/or a material deposition tool. These features of tool rack 4 make it possible to use materials prepared further in advance than would otherwise be possible, since they can be kept in favorable conditions for preservation by the cartridge until use. They also enable a greater level of automation, and more efficient use of materials than is otherwise possible because the materials can be automatically readied for use at the appropriate time, and possibly returned to storage conditions automatically by the system. Chemical reactions, cellular reproduction and metabolism, and other material properties can be monitored and controlled in materials awaiting use, enabling the controller evolution of material properties to be an integral part of the manufacturing plan.

Figure 3:
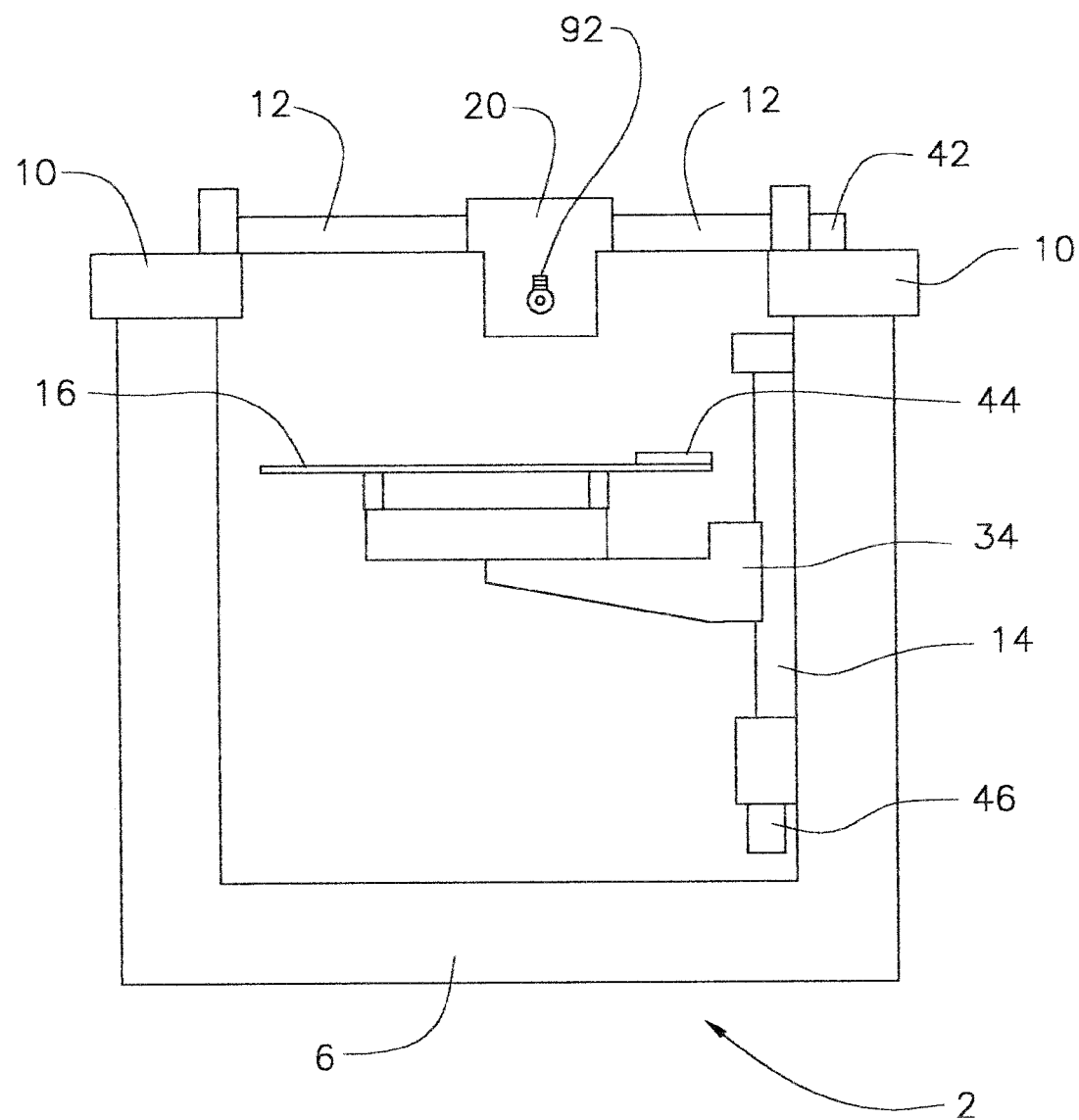
FIG. 3 is a front view of a material deposition device of a system in accordance with the present invention without a material deposition tool attached at the tool interface.

Turning to the illustration in FIG. 3, tool interface 20 is equipped with tool interface mount 92, which is capable of receiving a material deposition tool. Tool interface mount 92 is a standardized tool interface to accommodate a plurality of material deposition tools. In a preferred embodiment, tool interface mount 92 is a commercially available robotic tool changer that provides for a rigid, precise, and repeatable automatic mounting and unmounting of material deposition tools. Preferably, tool interface mount 92 has electrical connectors, fluid/gas connectors, and mechanical connectors (e.g., a pneumatic connection) capable of establishing electrical, fluid/gas, and mechanical communication with a connected material deposition tool. Thus, when a material deposition tool is connected to tool interface mount 92, electrical, fluid/gas, and mechanical communication may be established between tool interface 20 (and the system controller and any fluid, gas, electrical, and mechanical utilities available in the system) and the connected material deposition tool.

A unique feature of the system of the present invention is that rather than being dedicated to a single manufacturing process technology and to one or two materials, this system makes use of multiple deposition (and other manufacturing, testing, and measurement process) technologies, and an essentially unlimited number of materials. This is achieved by encapsulating a given manufacturing technology in a modular "tool" (referred to as a material deposition tool) which is manipulated by the material deposition device (i.e., positioning system 8) during the course of manufacturing, measuring, or testing an object. Tools may have significant onboard sensing, actuation and computational resources in order to monitor and control their own performance, and/or the state of the material that they are employing, as well as for communicating state information and control parameters with the system controller.

Material deposition tools useful in the system of the present invention (i.e., for positioning on tool interface mount 92) include, without limitation, various commercially available material deposition tools and material deposition tools described herein.

In one embodiment, one of the material deposition tools is a fusible-material extrusion tool for depositing thermally liquefied plastics, low melting-point metals, and other fusible materials. Fusible-material extrusion tools are commercially available. Typically, this type of tool employs motor-driven pinch-rollers to force feedstock material (in the form of a wire) into a heated portion of the tool and out of a constricted orifice (nozzle). The heated portion of the tool softens or melts the feedstock, permitting it to be pushed out of the nozzle as a fine stream of liquid or semi-liquid material. Nozzles are replaceable, and nozzle orifice diameters may be smaller than 0.010 of an inch.

Various modifications may be made to commercially available fusible-material extrusion tools for use with the system of the present invention. These design modifications may include a temperature sensor positioned directly in the nozzle, immediately proximate to the point where the material is deposited to control the extrusion temperature of the deposited material. In addition, the pinch-rollers may be modified to have a tooth shape which is optimized for minimal damage to the feedstock and maximum buckling strength of the feedstock as it is driven into the tool, allowing the feedstock to be driven with more force into the heater block and out of the nozzle. This modification permits faster extrusion rates and/or finer resolution (via narrower nozzles). In another modification, the body of the tool may be made of organic polymers to reduce the mass of the tool and thereby improve the performance of the positioning system while the tool is in use by the system. Also, the tool may be equipped with a muffler surrounding the feed stock material through which fluid or compressed gas may be circulated in order to actively cool the feedstock material after passing through the pinch roller and before reaching the heater block. This would also increase the buckling strength of the feedstock material and would allow for faster extrusion and/or higher resolution.

In another embodiment, one of the material deposition tools used in the system of the present invention is an ink-jet tool. Ink jet tools, in particular, and, more generally, any tool can be used to deposit multiple reactants into the same spatial location in order to effect a chemical reaction on a very local scale. The very small volumes achievable with ink-jet droplets (e.g. picoliters) are especially well suited to this. Ink-jet droplets of multiple reactants jetted into the same location will react very quickly, permitting the local control chemical reactions within deposited material, allowing very small scale structuring of chemical activity and resultant material properties. Reactant concentrations can be varied by relative numbers of drops of each type of reactant deposited at a give point. This can allow reactions fast enough that reactants do not have time to move (e.g., drip or flow) or evaporate or degrade before the reaction takes place. An ink-jet tool is capable of depositing multiple (e.g., four) materials simultaneously without material changes. An important benefit of ink-jetting for material deposition is high resolution (100 µm×100 nm disk-shaped deposit per droplet), especially when working with materials whose functionality depends on their being produced in thin films (e.g., semiconducting polymers, dielectrics, separator materials for batteries, electroding materials for actuators). The very small volume of droplets (picoliter) achievable with ink-jetting allows deposition of material onto non-planar surfaces. The very small droplets not only dry extremely quickly, but the small gravitational force they experience allows them to adhere to sloped and curved surfaces without the flowing that larger drops would experience. This is exceedingly valuable when fabricating articles with complex, non-planar geometries containing non-horizontal and/or non-planar laminae or other structures. The high resolution and point-by-point deposition of material permits structures (such as linear features whose material varies with length, or multi-material lattices) to be practically realized, making the products of an ink-jet tool complementary to those that can be achieved by a stream-type deposition tool such as a syringe tool (described below).

In a further embodiment, one of the material deposition tools is an electrospinning tool. An electrospinning tool uses an electrical potential difference between the material, generally a fluid, contained in the tool, and the substrate to draw the material out of the tool in extremely fine streams. This potential difference can be achieved by placing one electrode in contact with the fluid within the tool, and another electrode on the substrate (if it is conductive) or on a perforated electrically conductive plate placed between the tool and the substrate. A central hole in the latter plate is arranged concentrically with the outlet or nozzle of the tool so that the fluid stream may pass directly through and continue to be deposited on the substrate. Volatile liquid components of the material may evaporate from the stream of material because of electrostatic charging and self-repulsion and because of the very large surface area to volume ratio of the stream. The material which arrives at the substrate may thus be a dry thread of material with a diameter of nanometers. Adjusting the material composition, the spacing between the substrate and the tool, and the electrical potential can allow control of the liquid content and diameter of the deposited material. This type of tool permits the production of nanoscale structures, including highly aligned polymer molecules. Such a tool provides the system with the ability to embed materials structured at the nanometer scale into macroscopic objects being fabricated.

In another embodiment, one of the material deposition tools may be a "pick and place" robot tool. A "pick and place" robot tool is device which can hold, reorient, and accurately place an object onto a substrate. The materials dispensed by a "pick and place" robot tool may include integrated circuits, passive electrical components, electrical motors, batteries, and any other discrete solid objects with characteristic dimensions ranging from 100 micrometers to 10 centimeters. For example, a "pick and place" robot tool might place integrated circuit components onto conductive pads and conductive traces deposited by other material deposition tools in the course of fabricating an article. Still, other material deposition tools might then encapsulate the circuit components and conductive pads and traces in an insulating material to produce an article with embedded exogenously manufactured components.

In other embodiments, the material deposition tools may include, but not be limited to: thermal spray deposition tools, vapor deposition tools, and laser forward transfer deposition tools.

A thermal spray deposition tool is a device in which a solid material powder is entrained in a gas stream which is directed at the substrate. The stream is passed through a heat source prior to arriving at the substrate such that the powder particles are melted and deposited as tiny molten drops.

A vapor deposition tool employs a stream of gas to entrain vapor evaporated from a solid or liquid material contained in a heated reservoir. Within the tool, the gas stream flows past or through the reservoir, entrains the vapor, and is directed out of an orifice toward the substrate. When the substrate is below the condensation temperature of the vapor, the vapor will condense onto the substrate. The rate and morphology of deposited material can be regulated by varying the reservoir temperature, the gas stream velocity, and temperature, the substrate temperature, the orifice diameter, and the distance from orifice to substrate.

A laser forward transfer deposition tool employs a pulsed laser to transfer material from a source substrate to a receiving substrate. The source substrate is located between the laser and the receiving substrate. The source substrate generally consists of a laser transparent medium, such as a strip, tape, or disk of glass, fused silica, or polymer. The lower surface of the source substrate—that which faces the receiving substrate—is coated with a thin layer (e.g. 0.1-1000 micrometers) of the material to be deposited. A pulse from the laser is directed at the source substrate, passes through the transparent medium, and liberates a small quantity of the material attached to the source substrate medium. The momentum imparted to the material in the course of liberation carries it toward the receiving substrate, where it is deposited. After each laser pulse, the relative position of the source substrate and the laser are changed so that a region of the source substrate which has not received a pulse, and hence retains its full coating of material to be deposited, is placed in the path between the laser and the desired point of deposition on the receiving substrate.

The system may also include material modification tools which are intended to modify the properties and/or geometry of material after it has been deposited by a material deposition tool. Material modification tools include, but are not limited to, lasers, infrared lamps, ultraviolet lamps, cutting tools, milling tools, drills, temperature controlled jets of gases and/or fluids and/or gas or fluid entrained powders. In addition, any material deposition tool may also be integrated with and/or mounted simultaneously with other material deposition tools, and/or material modification tools, and/or material sensing apparatus. These combination tools and combinations of tools allow the deposition and/or modification and/or measurement of one or more deposited materials in very rapid succession. This enhances the spatiotemporal control of the system over the materials being deposited.

Figure 4:
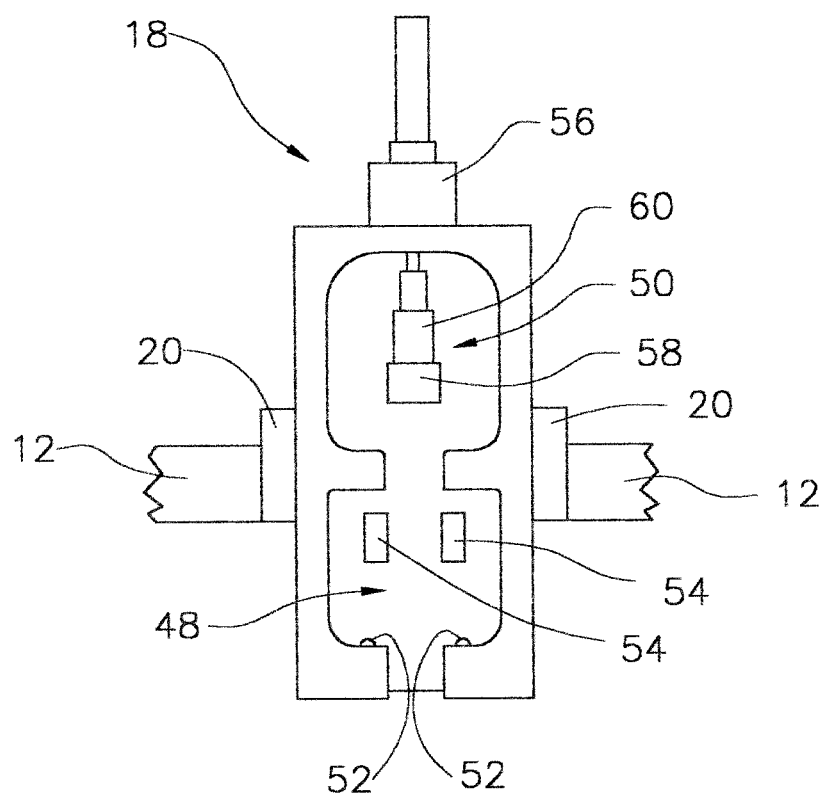
FIG. 4 is a front view of a material deposition tool in accordance with the present invention, which is a cartridge holding tool capable of receiving a modular material cartridge.

In yet another embodiment, one of the material deposition tools is a cartridge holding tool capable of receiving a modular material cartridge. FIG. 4 illustrates a preferred embodiment of material deposition tool 18, which is a cartridge holding tool equipped with cartridge socket 48 for receiving a modular material cartridge. As shown in detail in FIG. 4, cartridge socket 48 has mechanical interfaces 52 that hold a material cartridge in cartridge socket 48 and/or embedded intelligence in the material deposition tool and/or the system controller. Electronic and fluid/gas interfaces 54 establish electronic communication between the material cartridge placed in cartridge socket 48 and the system controller and provide fluid/gas flows to the material cartridge which may be used by the system controller and/or embedded intelligence in the tool and/or in the cartridge to monitor and control the state of the cartridge, and/or the material or materials contained in the cartridge. This enhances the ability of the overall system to achieve spatiotemporal control of the evolution of material properties before, during, and after fabrication of an article. Fluid/gas flows may also be used in a supporting role for fabrication by being routed through the cartridge and directed downward toward the substrate. This allows the creation of a highly localized controlled environment at the point of material deposition e.g. with an inert gas flow to prevent chemical reactions.

In a preferred embodiment, material deposition tools of the present invention are operably connected to the system controller, whether they are attached to the tool interface or not.

In the particular embodiment shown in FIG. 4, material deposition tool 18 is equipped with a volumetrically controlled dispensing system having linear motor 56 which provides up and down force to linear shaft 50, thus driving the dispensing of material from material deposition tool 18. As described in greater detail below, motor 56 is controlled by a system controller. Linear shaft 50 has load cell 60 and electromagnet 58. Load cell 60 and electromagnet 58 are placed in linear shaft 50 to provide control to the deposition of material from a material cartridge located in cartridge socket 48 via sensor communication with the system controller. The load cell allows the system controller and/or any intelligence and control embedded within the tool and/or within the cartridge to monitor and/or regulate the pressure being applied by the motor via the plunger and piston to the material within the syringe. This may be done in order to achieve a desired flow of material from the cartridge. The electromagnet allows the system controller to selectively engage or release a mechanical connection between the motor and the plunger. According to the command of the system controller, when the electromagnet is energized, this allows the plunger to remain engaged to the motor regardless of whether the motor is moving upward or downward. When, according to the command of the system controller, the electromagnet is not energized, the cartridge may be easily removed from the cartridge socket, and replaced. In a preferred embodiment, the underside surface of electromagnet 58 is equipped with a contact sensor which monitors contact between electromagnet 58 and a syringe from a material cartridge and relays the information to the system controller.

Figure 5:
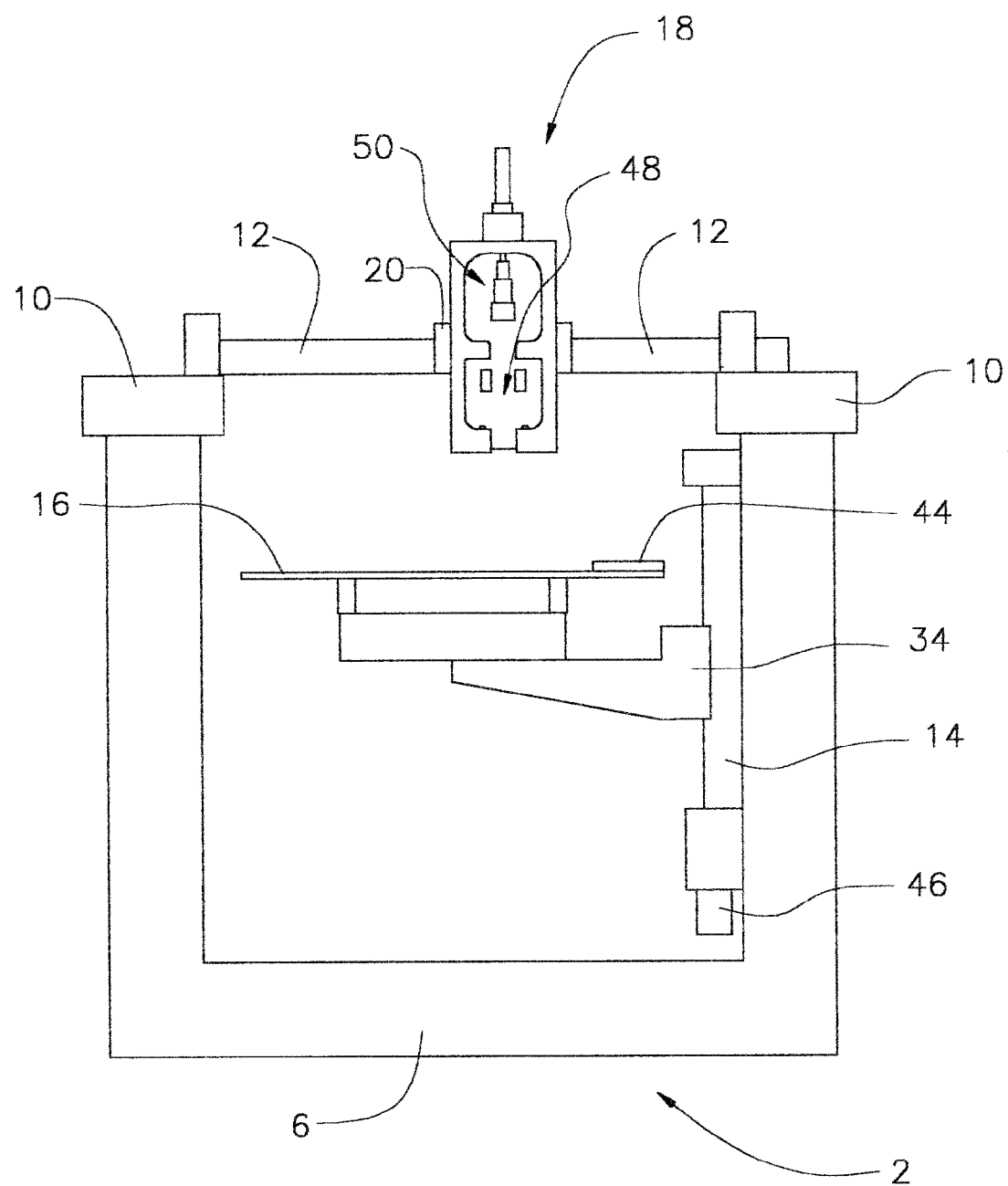
FIG. 5 is a front view of a material deposition device in accordance with the present invention fitted at a tool interface with a cartridge holding tool capable of receiving a modular material cartridge.

FIG. 5 shows the material deposition tool of FIG. 4 attached to tool interface 20 of material deposition device 2 of the system of the present invention.

Figure 6:
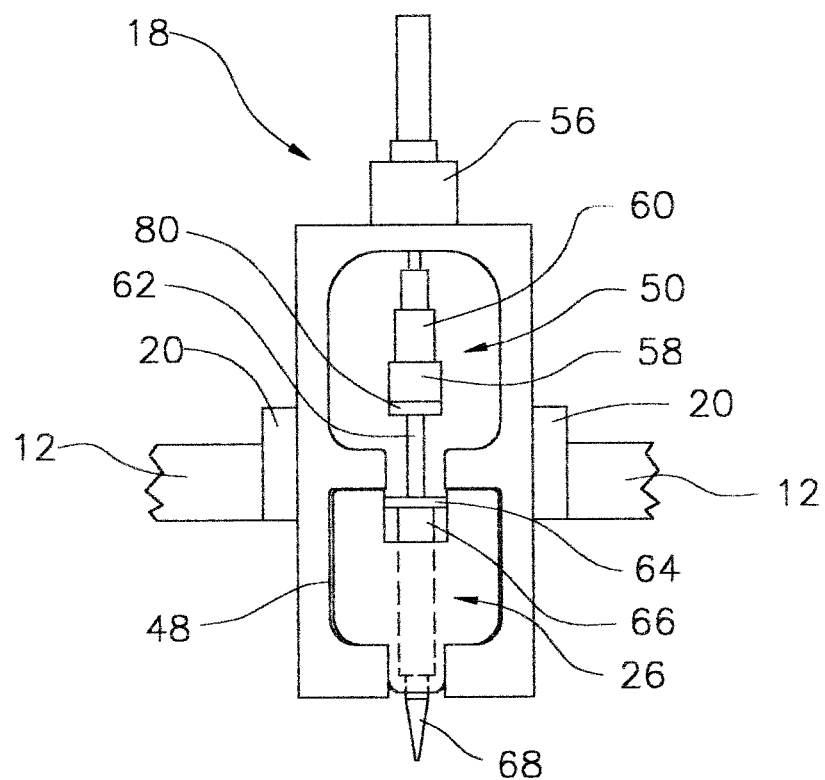
FIG. 6 is a front view of a cartridge holding tool in which a modular material cartridge carrying a syringe is positioned in the cartridge chamber.

FIG. 6 illustrates a material deposition tool, which is a cartridge holding tool, loaded with material cartridge 26 in cartridge socket 48. Cartridge 26 holds syringe 66 that contains material to be deposited through syringe needle 68. Plunger 62 is inserted into syringe 66 at opening 64 and provides the force by which material exits syringe needle 68. Plunger disk 80 at the top of plunger 62 is, in a preferred embodiment, a magnetically permeable steel disk capable of forming a magnetic connection with electromagnet 58. The magnetic connection allows material flow from cartridge 26 to be controlled by linear motor 56 of material deposition tool 18.

Figure 7:
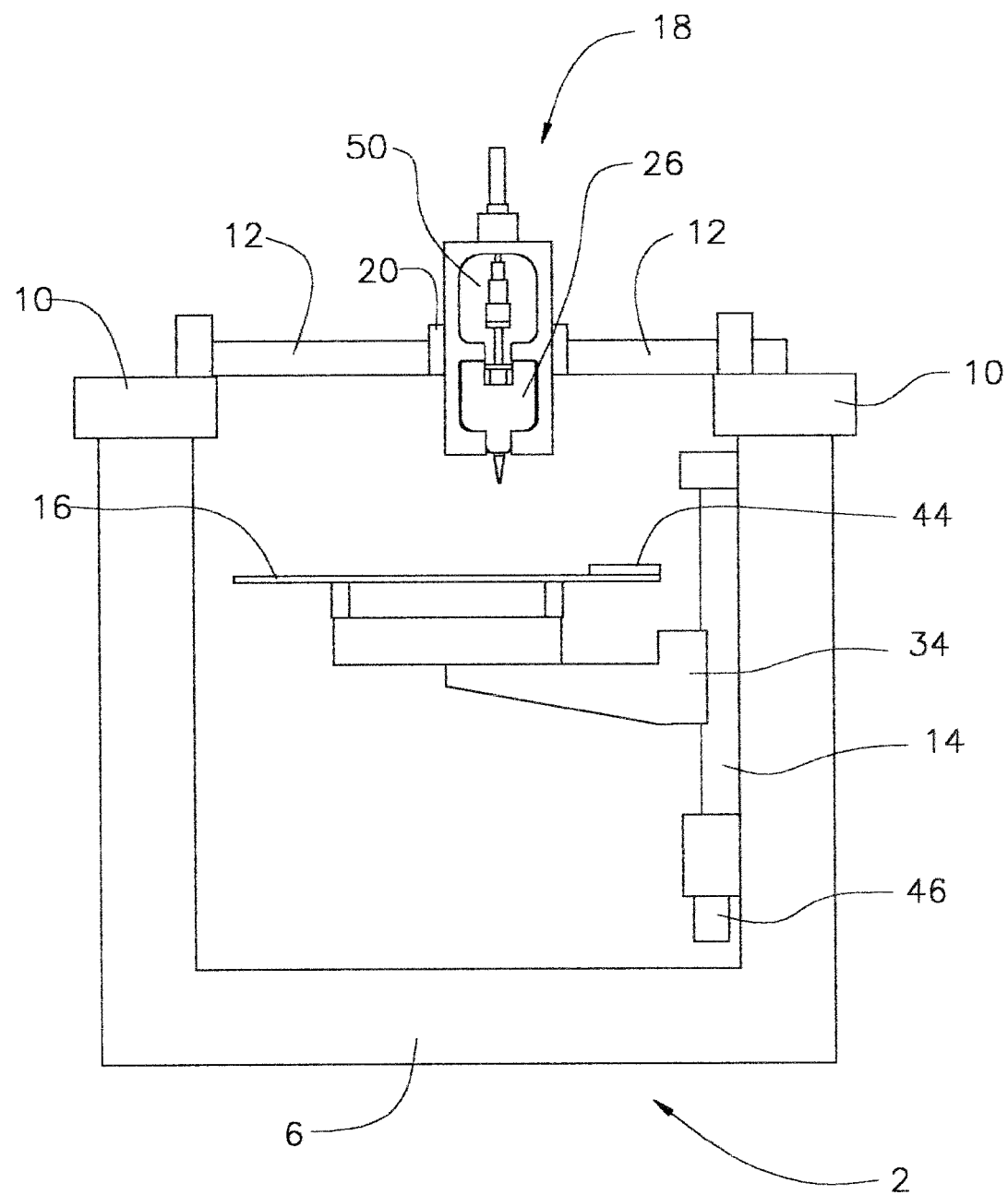
FIG. 7 is a front view of a material deposition device of a system in accordance with the present invention fitted at the tool interface with a cartridge holding tool in which a modular material cartridge carrying a syringe is positioned in the cartridge chamber.

FIG. 7 shows the material deposition tool of FIG. 6 attached to tool interface 20 of material deposition device 2 of the system of the present invention.

Figure 8A:
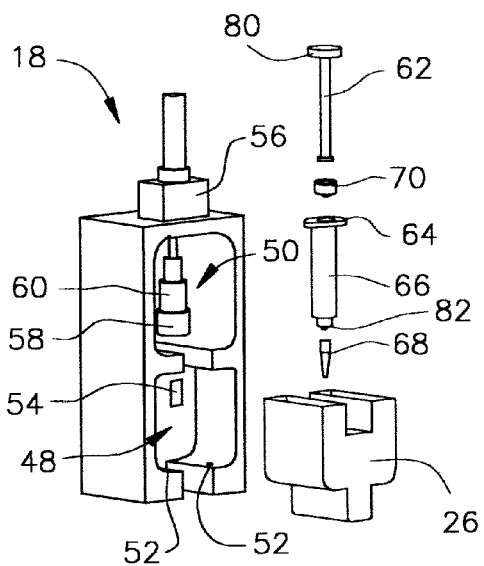
FIGS. 8A-D are perspective views of a cartridge holding tool and material modular syringe cartridge that fits into the cartridge holding tool.
Figure 8B:
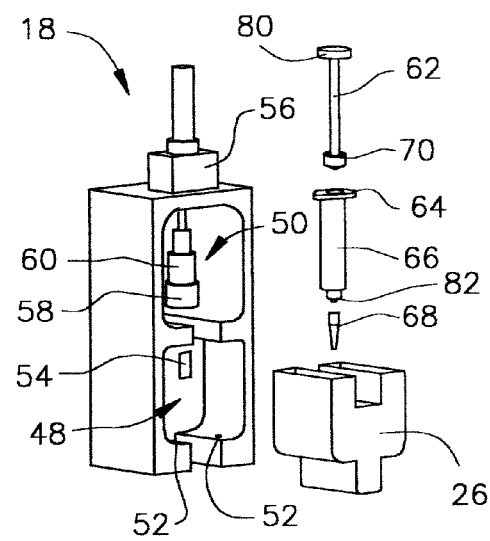

A detailed illustration of how a preferred syringe cartridge is assembled and loaded into a cartridge holding tool is illustrated in FIGS. 8A-D. FIG. 8A shows the various component parts of a syringe that fits into syringe cartridge 26. These parts include syringe 66 with opening 64 at the top, syringe needle 68 which is connected to the bottom of syringe 66, and piston 70, which connects to plunger 62 (FIG. 8B). Syringe 66 and piston 70 are preferably disposable, whereas plunger 62 is preferably reusable.

To prepare the syringe for loading into cartridge 26, syringe 66 is filled with material, typically by pumping material in via Luer-lock tip 82 of syringe 66. This minimizes the amount of trapped air in syringe 66, which improves the ability of the system to control the dispensing of the material. Syringe needle 68 is then mounted on syringe 66.

Figure 8C:
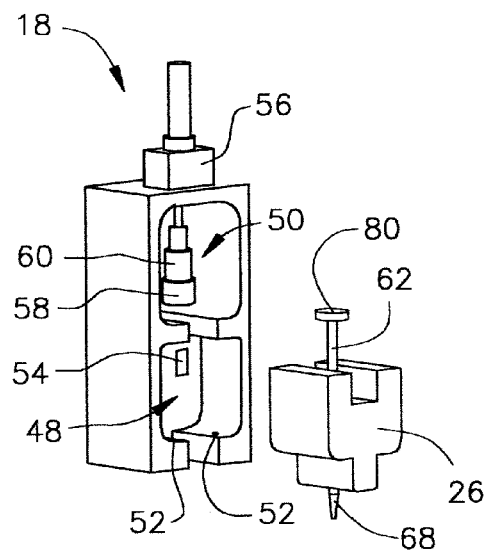
Figure 8D:
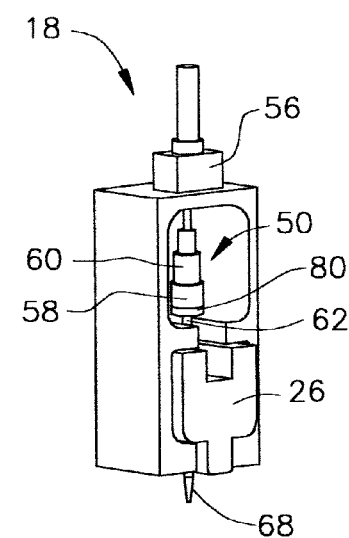

A syringe loaded with material is inserted into an opening in material cartridge 26, as illustrated in FIG. 8C. As shown in FIG. 8D, material cartridge 26 is then inserted into cartridge socket 48 of material deposition tool 18. In this position, electromagnet 58 is brought into magnetic contact with plunger disk 80. Once material deposition tool 18 is loaded with syringe cartridge 26 it may be loaded onto tool rack 4 or onto tool interface 20 of positioning system 8.

In a preferred embodiment, syringe cartridge 26 is equipped with active elements that can monitor and control the state of the material in syringe 66 residing in syringe cartridge 26 and can communicate this information to the system controller, or be programmed or controlled by the system controller or user, via cartridge electronic interfaces 54. Syringe cartridge 26 may also contain auxiliary material interfaces 74, which mate to auxiliary material interfaces in cartridge socket 48 of cartridge holding tool 18. These interfaces allow syringe cartridge 26 to be supplied with auxiliary materials such as fluids, gases, or powders which may be used within the cartridge to monitor and/or control the state of the material contained in cartridge 26, or be directed via or by the cartridge downward onto the substrate and/or along the stream of material which is being deposited. In the latter case, these auxiliary materials may be used to control the evolution of material properties after the material has been deposited. For example, heated air may be used to accelerate evaporation of volatile materials, vacuum may be used to draw away undesirable fumes or byproducts, inert or reactive gases may be delivered to the point of material deposition to prevent or promote reactions. This communication will be routed through electronic interfaces in cartridge socket 48, or wirelessly communicated directly to the system controller and/or cartridge holding tool 18 when syringe cartridge 26 is mounted in cartridge socket 48 of cartridge holding tool 18, or through tool rack 4 when syringe cartridge 26 is positioned on tool mount 28 of tool rack 4 and is waiting to be loaded into cartridge holding tool 18 for use. In either case, syringe cartridge 26 will be informed of what type of material it is loaded with and syringe cartridge 26 will begin to monitor and control the material state. The status information will be communicated to the system controller so that accurate material data can be used in manufacturing planning and material deposition control.

When cartridge holding tool 18 is mounted on tool interface 20 and is not yet holding a material cartridge, an appropriate cartridge can be taken from cartridge holding device 32 of storage rack 4 and inserted into cartridge socket 48 of cartridge holding tool 18 either by transfer device 100 or by a user. Linear motor 56 will then move downward until electromagnet 58 detects contact with plunger disk 80. Electromagnet 58 is energized, locking the syringe plunger disk to the linear motor shaft.

To dispense material from syringe cartridge 26 onto substrate 16, the system controller commands positioning system 8 to move material deposition tool 18 so that syringe needle 68 traces out the appropriate curvilinear paths, while simultaneously commanding material deposition tool 18 to dispense material.

The fact that material cartridges may contain active components, computational hardware, and communication ability provides for additional modes of control over the deposition of materials from material deposition device 18, as well as allowing control of the state of the material while it resides within a cartridge. It also permits the use of a wider variety of materials than would otherwise be amenable to deposition. Cartridges may contain magnetic stirring or a vibrational stirring apparatus which can be used to maintain homogeneity in materials (e.g. multi-phase slurries, emulsions, dispersions) that otherwise would separate or settle, causing clogging of the tool or undesirable dispensing properties. Heating and cooling devices within syringe cartridge 26 may be used to manage viscosity of materials and to promote or prevent chemical or biological activity. In this way, materials can be maintained within syringe cartridge 26 in one state which is desirable for one set of reasons, then allowed to evolve into a different state after deposition. Given that the entire system of the present invention may reside in an enclosure (described below) which allows environmental control—humidity, temperature, gas mix, lighting, sterility—sophisticated control over the trajectories of many material parameters through time can be achieved, even as the material is deposited in precisely controlled geometry.

It is possible to use the control that the active cartridge and the enclosure environment provides over the material state before, during, and after the deposition process to perform feedback control of parameters of the deposited material other than geometry—enabling a steering of the manufacturing process toward a final product which more closely matches that desired. This can include such parameters as color, reflectivity, sterility, (biological) viability, mechanical properties, reactivity, odor, etc., provided that some means of detecting these parameters can be provided to the system. This means may consist of a human expert and/or an appropriate automatic sensor mounted on the material deposition tool or embodied as a separate modular sensing tool, for sequential use. Appropriate sensors include, without limitation, CCD cameras with machine vision software, "electronic nose," mechanical probes with force instrumentation, and fluorescence CCD microscopes with machine vision software.

An alternative to sensing of these properties via a tool or sensor mounted on tool interface 20 (or material deposition tool 18) is to deposit the materials directly onto a sensing apparatus, or to embed the sensing apparatus within the material as it is being deposited. These substrate or embeddable sensors include, without limitation, biochip sensors for detection of biological products and monitoring and control of living cells and tissues, temperature sensors, semiconductor chemical sensors, strain gauges, pressure sensors, and many others.

Because most of the material deposition tools which are used with the system of the present invention deposit materials through an orifice of some kind, there is the frequent occurrence of residual material accumulating around the orifice, nozzle, tip, etc. Maintaining precise control of the deposition process, desired segregation of materials, and avoiding clogging and damage to tools and objects being fabricated, all require that the tools be cleaned periodically to remove this residual material. Several approaches may be used in the system to achieve this cleaning automatically. For tools with robust tips or nozzles and stubborn material accumulations, a wire brush, rubber scraper blade, solvent-saturated sponge, or a combination of these may be employed, namely by having positioning system 8 drive material deposition tool 18 to a point on substrate 16 where these devices are mounted, then rubbing the tip of material deposition tool 18 (or syringe cartridge 26) against them automatically. For more delicate tool tips, such as fine gauge needles, a solvent bath and/or a gas jet may be used in an analogous fashion to wash or blow material away. Because the various material deposition tools used in the system may span all of these needs, in general, several tip cleaning devices will be positioned at the edge of the substrate.

Figure 9:
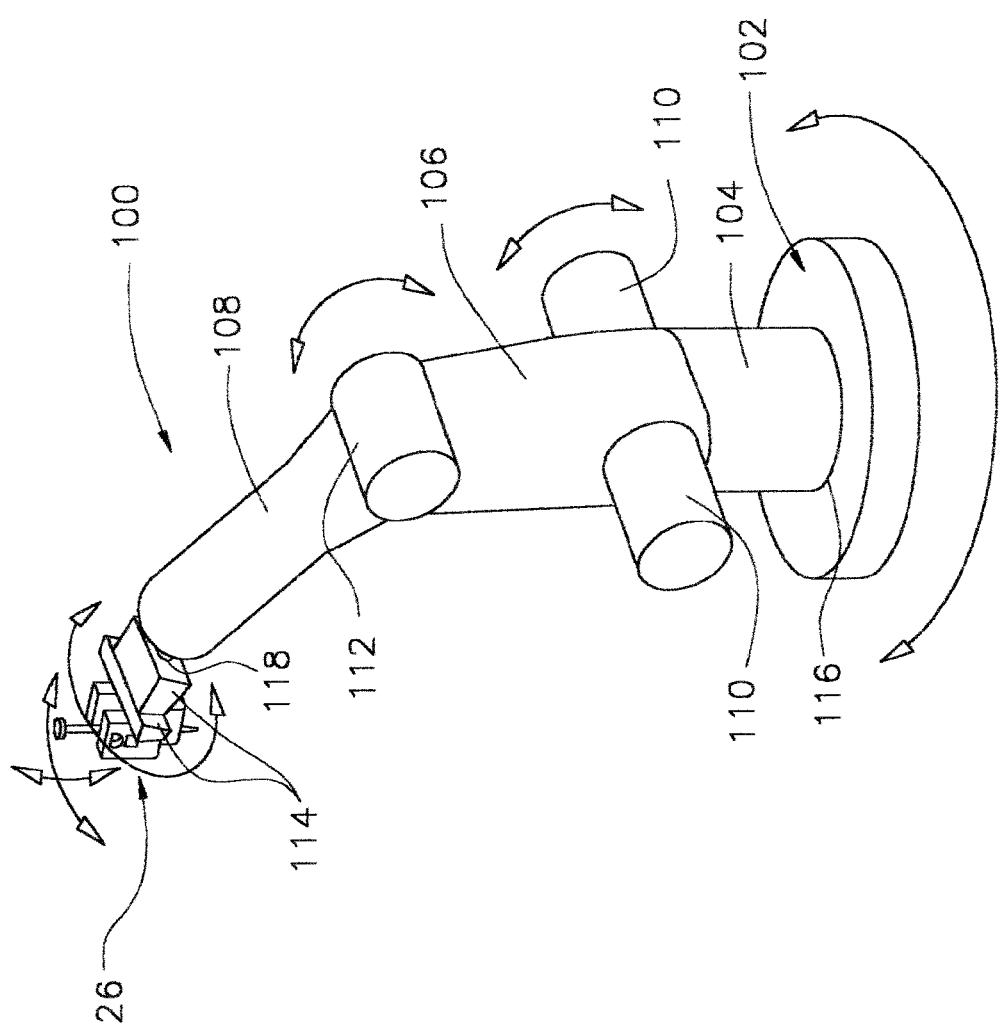
FIG. 9 is a perspective view of a transfer device in accordance with the present invention.

Turning to FIG. 9, in one embodiment, transfer of material deposition tools and/or substrate modules and/or material cartridges to and from the tool rack and/or other storage locations and the material deposition device is carried out by transfer device 100. In a preferred embodiment, transfer device 100 is a six-axis robotic arm. Transfer device 100 is positioned on base 102 and extends from base 102 by various sections connected by axes. In particular, section 104 is connected at base 102 by axis 116, which permits section 104 to swivel axially relative to base 102. Section 104 is connected to section 106 by axis 110, which allows pivotal motion of section 106 relative to section 104. Likewise, section 108 pivots relative to section 106 at axis 112. Section 108 is connected to tool grip 114 at connection 118. Connection 118 permits tool grip 114 to have three ranges of motion relative to section 108. These ranges of motion include a side to side horizontal range of motion, a vertical up and down motion, and an axial swivel motion. In the illustration of FIG. 9, tool grip 114 is connected to material cartridge 26. In other embodiments, the transfer device may be a conveyer belt, carousel, or human operator.

Transfer device 100 makes it possible to automatically change material deposition tools during the course of manufacturing a product. This greatly expands the range of products that the system of the present invention can produce relative to a traditional freeform fabrication system and further allows for upgradeability and customization of the system and its product space, with new or specialized technologies for manufacturing, testing, and measuring products easily incorporated as new or additional tools. Transfer device 100 may also be equipped with various sensors and feedback controls which communicate with the system controller.

Figure 10:
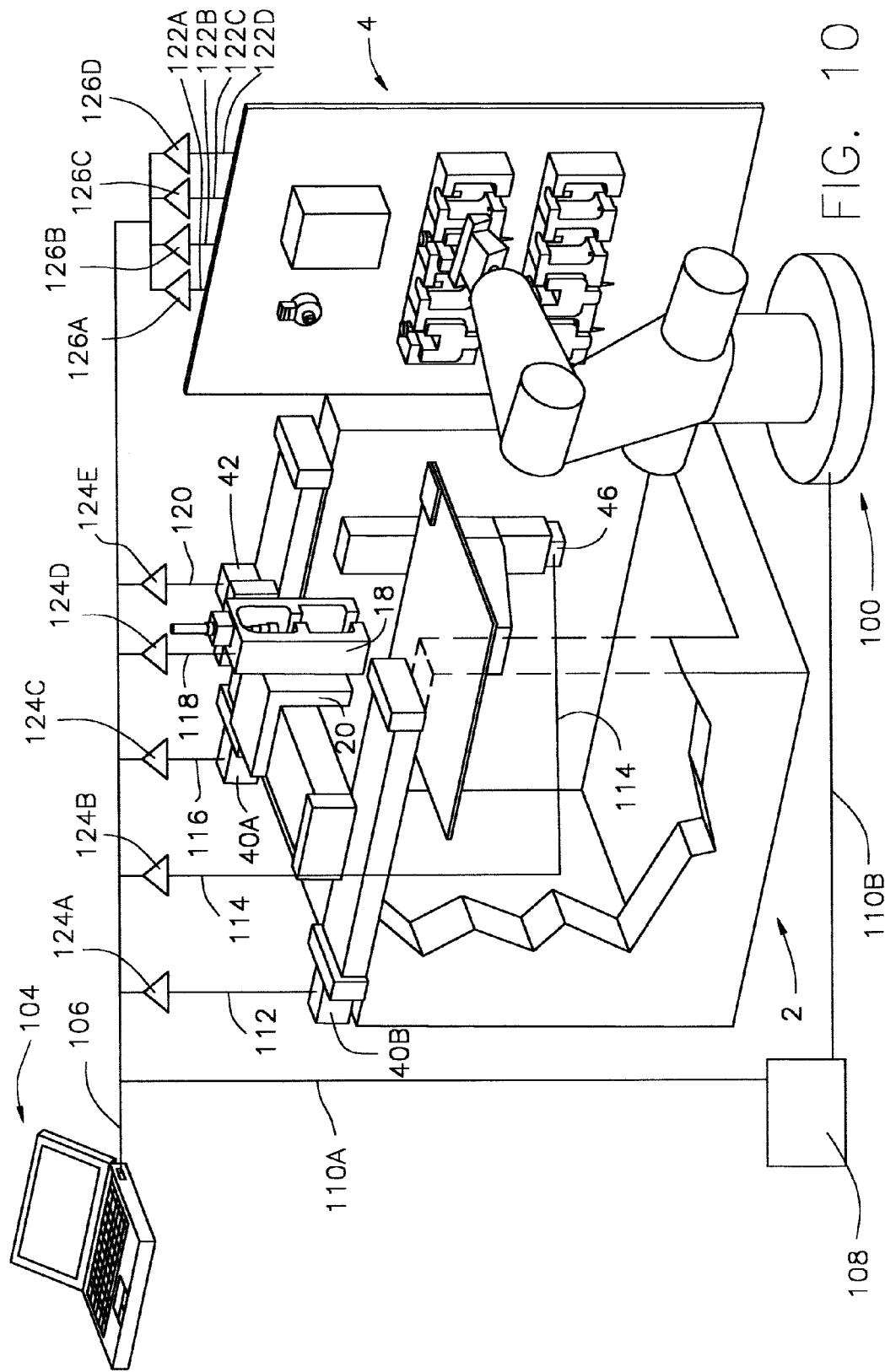
FIG. 10 is a perspective view of a fabrication system in accordance with the present invention in which the transfer device is in contact with a material deposition tool located on a tool rack. Also shown is the electronic wiring of a fabrication system that connects to an external computer.
Figure 11:
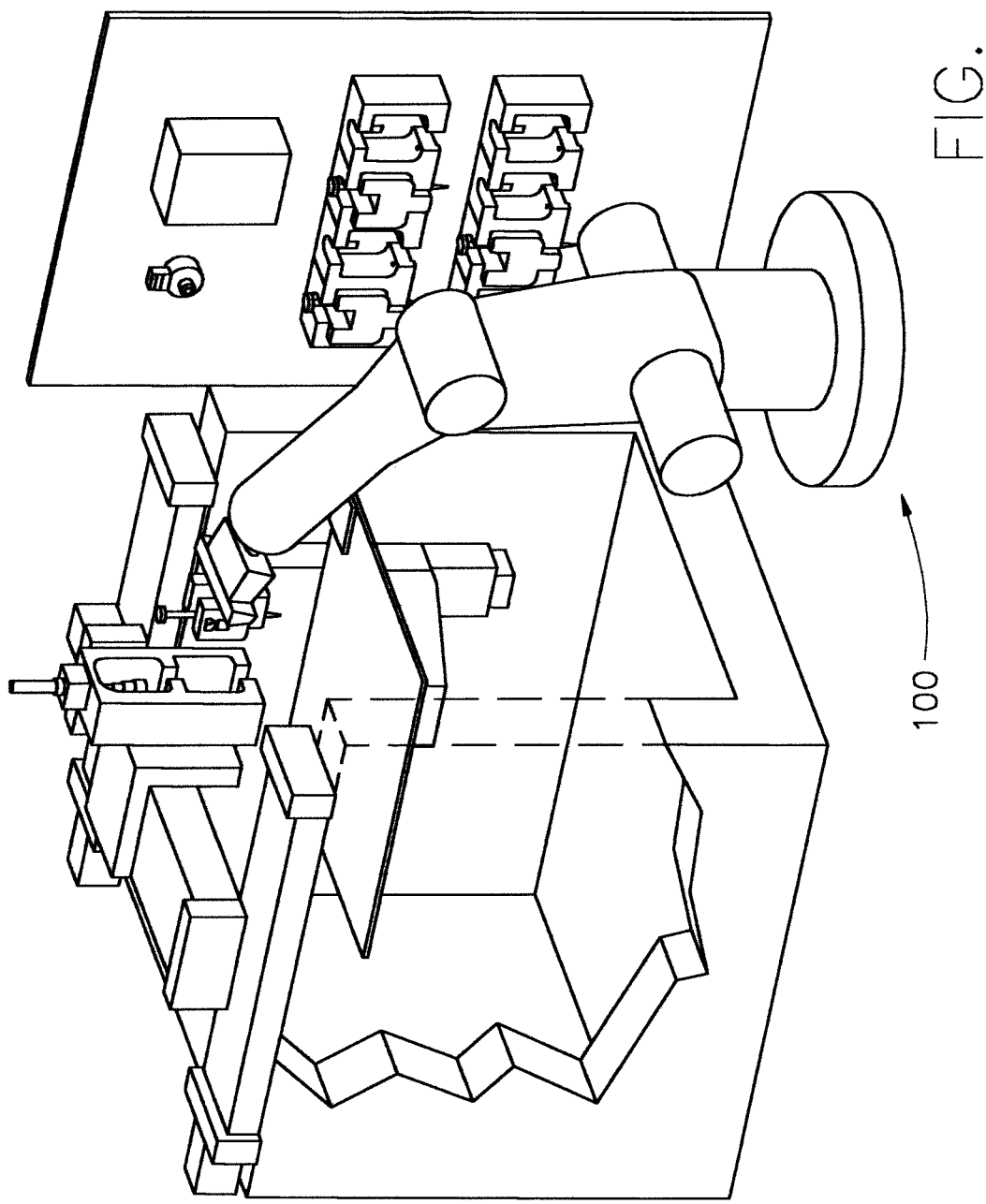
FIG. 11 is a perspective view of a fabrication system in accordance with the present invention in which a transfer device is replacing a material cartridge in a cartridge socket of a material deposition tool connected to a tool interface.

Operation of the system of the present invention is controlled by a system controller operably connected to the material deposition device and the transfer device. In addition, the system controller may also be connected to the tool rack and directly to the material deposition tools. FIG. 10 illustrates the system of the present invention with electrical connections to system controller 104, which is an external computer. Electrical line 106 extends from computer 104 and provides an electrical connection between the system controller (i.e., external computer 104) and various motors and sensors that operate the system of the present invention. In particular, electrical line 110A provides an electrical connection from external computer 104 to controller/amplifier 108 which, in a preferred embodiment, is a "smart amplifier." Controller/amplifier 108 is electrically connected to transfer device 100 by electrical line 110B. Movement of transfer device 100 is controlled by controller/amplifier 108 and external computer 104. These electrical connections allow placement of a material deposition tool onto tool interface mount 92 and removal of a material deposition tool from tool interface mount 92 by transfer device 100 (see FIG. 11).

Also shown in FIG. 10 are the electrical connections between motors that drive positioning system 8 and external computer 104. Electrical lines 116 and 112 provide electrical connection between motors 40A-B, respectively. Likewise, motors 42 and 46 are connected to external computer 104 via electrical lines 120 and 114, respectively. Electrical line 118 provides an electrical connection between external computer 104 and material deposition tool 18. Typically, the electrical connection between the material deposition tool and external computer 104 involves controlling the dispensing of material from material deposition tool 18, but may also provide communication between the system controller and any embedded intelligence, and/or actuators, and/or sensors positioned on material deposition tool 18 and/or on syringe cartridge 26, and/or on any material modification tools also present in the system, which are described in greater detail below. Electrical connections may also be made between tool interface 20 and external computer 104.

In a preferred embodiment, electrical lines 112, 114, 116, 118, and 120 are connected to amplifiers 124A-E, respectively, to provide additional power to perform mechanical operations.

Electrical connection is also preferably made between tool rack 4 and external computer 104 via electrical lines 122A-D which are further preferably powered by amplifiers 126A-D, respectively. These electrical connections receive information from tool rack 4 and relay it back to external computer 104.

Fabrication of a product using the system of the present invention is carried out as material is deposited from material deposition tool 18 in a pattern on substrate 16. The pattern is established by the system controller, which operates according to an electronic data file so that changes to the product only require changes to the design data of the system controller. In its basic operation, transfer device 100, according to a manufacturing plan programmed into the system controller, takes a specified tool from tool rack 4 and connects it to tool interface 20. Tool interface 20 then communicates with material deposition tool 18 and configures it for use. Material deposition device 2 then performs some steps in the manufacturing plan, e.g. depositing some material in a designated pattern along substrate 16. Transfer device 100 then retrieves material deposition tool 18 from tool interface 20 and returns it to tool rack 4.

System controller 104 is operated by fabrication system software that automatically converts design data into a manufacturing plan. The fabrication system software automates the majority of operations of the system of the present invention, permitting the designer's intent to be converted into a realized product with a minimum of labor and prerequisite specialized knowledge about the materials being used (i.e. deposited). System controller 104 is designed to store data about system performance and to improve the system automatically by updating data and models which it uses for manufacturing planning, manufacturing simulation, manufacturing plan execution, and operation control.

The main components of the system software of system controller 104 are the manufacturing planning, operation control, materials/tools/substrates database, and design database. The manufacturing planning software is responsible for converting the designer's intent, via the product description data, into an executable plan for producing the design. In the simplest implementation, the system expects the product description data to be the geometry of the product, with contiguous subregions of geometry (called "chunks") labeled with the material which the designer desires for that subregion, and the tool used to deposit that material. For each chunk of geometry, the materials/tools/substrates database is queried by the planning software for specifications of the material deposits that the requested material/tool combination can provide. These specifications include the geometry of the "atomic" deposits of material that this combination can produce. When the material deposition tool is an ink-jet tool, the atomic deposit is a deposit caused by a single drop of material from the tool. For other material deposition tools, such as a syringe tool and a fusible material extrusion tool, the atomic deposit may be curvilinear with some minimum length and some nominal cross-section dimensions. Still other atomic deposit types are possible with other material deposition tools, and many tools are capable of producing individual deposits of various sizes and shapes. The simplest manufacturing planning implementation does not take advantage of this. The essential aspect of the atomic deposit is that it can be combined into larger deposits by contiguous placement without producing undesirable loss of properties in the large deposit relative to those of the atomic deposit. The chunk geometry is decomposed into a union of geometric solids whose form is dictated by the atomic deposit. Positions (and possibly paths) in 3-dimensional space are stored for these to be later used to specify the paths and/or coordinates (referred to as the "set of paths," or "toolpaths") for material deposition to be performed by the system. When decomposition has been performed for all chunks in the design, the full set of data describing these decompositions is automatically sorted to satisfy a multiple objective optimization of the manufacturing process. This sorted set of paths (with associated tool and material labels and coordinates) constitutes a manufacturing plan which is executable by the system control software and system hardware.

In the simplest approach, the sorting of paths will arrange the toolpaths by vertical (Z-axis) coordinate and paths with the same vertical coordinate will be grouped by material/tool combination. More sophisticated optimizations take into account more detailed information about the materials, tools, performance of the system itself, and known design rules (e.g. from the design database) for certain aspects of the design. More sophisticated optimizations can also involve optimizing the shape and directionality of material deposition paths to achieve desired properties in the finished products. This can include optimizing mechanical properties such as tensile strength along primary stress axes, or possibly even along 3-dimensional curves through an object being fabricated. This type of final material property optimization through path optimization can also be used to provide preferential axes for tissue growth when working with living biological materials. Information to drive these optimizations can be extracted from the materials/tools/substrates and design databases, from real-time and historical performance data that the system maintains about itself, and from a simulation of the manufacturing process. This latter method becomes more crucial as designs, material behavior, and material interactions become more complex, and specifications for the finished product become more stringent. The simulation may make use of models of material evolution over time and in response to environmental conditions which are stored in the materials/tools/substrates database, models of system operation and performance, and may perform physical simulations of a candidate manufacturing process for a given design (including finite element models, or other physics-based modeling). In this way, the system can make predictions about the quality and/or performance of a final product that might result from a given manufacturing plan, which can then be used for automated searching for manufacturing plans which satisfy the objective functions supplied by a user in the design specifications for the object to be produced. The simulation, in an interactive mode, can permit a designer to explore the effect of alternative designs on the complexity of the manufacturing process. The simulation of the manufacturing process also plays an essential role for error recovery/correction during a manufacturing process. Error recovery/correction is important because producing complex objects with novel or experimental materials is costly and time consuming. Further, if the system does not detect and recover from errors during the manufacturing process, the errors will—by the very nature of the SFF process—be buried within the object being produced and be difficult or impossible to diagnose and repair. The manufacturing simulation allows the system, at any step in the manufacturing process, to compare the state (geometry and other automatically detectable properties) of the simulation to the state of the real object being produced as measured by 3-D scanning (or other) sensors. Discrepancies can be remedied by generating modifications to the manufacturing plan which replace or circumvent the error—these too can be explored in simulation, and the effect of the errors and the modifications to the manufacturing plans can be used to update predictions of the quality and performance of the final product.

The manufacturing planning software can include special purpose data conversion capabilities to assist the designer in conveying design data to the system. This can include automatic conversion of computed tomography and magnetic resonance imaging data into manufacturing plan geometry data, or automatic conversion of point cloud data resulting from non-contact scanning directly into manufacturing plan geometry data.

Another element of the system controller of the present invention is operation control, which includes all of the feedback control, self-testing, data-collection software required to operate the system hardware and execute a manufacturing plan produced by the manufacturing planning software, including: (i) low-level control software for tools and material cartridges which may be executed by computational hardware within the tools and cartridges themselves; (ii) the feedback control laws which operate the environmental controls within the system enclosure; (iii) the motion control software that commands the positioning systems and coordinates positioning system control with tool deposition control; (iv) control and path planning for the transfer device used for tool and material changes; and (v) scanning sensor control, data collection, and data conversion.

The materials/tools/substrates database component of the system controller is used to store information about the properties of materials used in fabrication, the types and shapes of deposits of material that can be made by a given deposition tool, specialized parameters for controlling deposition tools to achieve each type of deposit, selection and parameters for controlling material modification tools to achieve a desired modification of material properties, parameters for controlling substrate modules in order to achieve a desired trajectory of materials properties evolution, material interactions with other materials, and other information. The material properties information may be in the form of a complex material model, which can include time evolution of the material properties in response to conditions. This type of information may be used in many ways in manufacturing planning and manufacturing simulation, including: (i) generating plans for the control of material substrate modules and enclosure environmental conditions to guide the evolution of material properties before, during, and after deposition (e.g. cellular reproduction rates, chemical reaction rates, etc.); (ii) identifying complications in a manufacturing plan, e.g. where adjacent materials might be reactive, where a liquid might need to be deposited only after a solid boundary has been constructed to contain it; and (iii) identifying how long manufacturing plan steps must be spaced by in order to allow deposited materials to solidify, react, etc.

The information in the database is compiled from a variety of sources. First, the embedded intelligence, sensing, and communications in material deposition tools and cartridges obtains real-time information on quantity and status of materials loaded into the system for use in the current manufacturing plan, and health and operational status of the tools. Second, chemical or materials data references and research obtain general chemical and materials properties data and dynamic properties models. Third, manual calibration by operators or machine learning algorithms within the system (Malone et al., "Application of Machine Learning Methods to the Open-Loop Control of a Freeform Fabrication System," *Proceedings of the* 15*th Solid Freeform Fabrication Symposium*, Austin Tex., August 2004, pp. 377-388, which is hereby incorporated by reference in its entirety) retrieve tool control parameters required to generate a given material deposit geometry.

The design database is a repository of subunits of manufacturing plans and design rules of thumb that have been demonstrated to be successful, as well as complete designs and manufacturing plans for useful functional modules that are likely to be desirable inclusions into other designs. Maintaining this database is important, because no practical manufacturing simulation will be able to predict all issues of concern during manufacturing. The successful designs, rules, tricks, and modules capture much of the hidden information that would be difficult or impossible to simulate.

Modules can be complete functional devices, such as batteries, actuators, joints, transistors, etc., which can be freeform fabricated directly into other designs to produce a composition of higher functionality. Design rules can be empirical relations between, for instance, the volume of active material deposited in a certain type of device, and the performance of the resulting device.

In order for the manufacturing planning and control system to be able to automatically monitor the progress of a fabrication operation, to identify and locate objects placed in the build environment, and to measure the geometry of the finished product, the system may include a non-contact ranging sensor device which can be scanned by the positioning system across the build surface (i.e. substrate). This device has a distance resolution of 10 micrometers, while the positioning system has an XY-plane resolution of 5 micrometers. The benefit of this type of sensor is that it is compact enough to embed within material deposition tools near the point of material deposition (e.g. nozzle), and of low enough cost to use in each cartridge, even in multiples. The presence of the ranging sensor within a material deposition tool permits the acquisition of the geometry of deposited material with minimal interruption of the fabrication process (e.g. without pausing manufacturing in order to mount a separate sensing tool to perform the scanning) and very near the point of deposition. This improves the value of the resulting data for use in feedback control of the deposition tool—geometric flaws in deposited material can be detected quickly, minimally allowing the manufacturing planning software to design compensating material deposits which can be executed in a timely fashion, without compromising the properties of materials which are sensitive to the time since deposition. If such sensing can be provided in a 360 degree circle around and very proximate to the point of deposition, such sensing could be used for online feedback control of the deposition tool— allowing the control law for the tool to adjust tool actuator commands in order to achieve the desired deposit geometry. Because many materials are not mechanically durable, and many are liquids, measurement by contact methods is not acceptable for this role. Even if not useful for online feedback control, more frequent "semi-online" feedback provided by the currently employed sensor greatly improves the achievable final quality of the object being fabricated, because it allows the manufacturing planning software to compensate for variability in the properties of the materials being employed, or other deposition errors by automatically generating modified manufacturing plans which compensate for the errors, for instance by depositing material into undesired gaps, or by modifying subsequent deposition paths so that they do not collide with excess material that was accidentally deposited.

Figure 12:
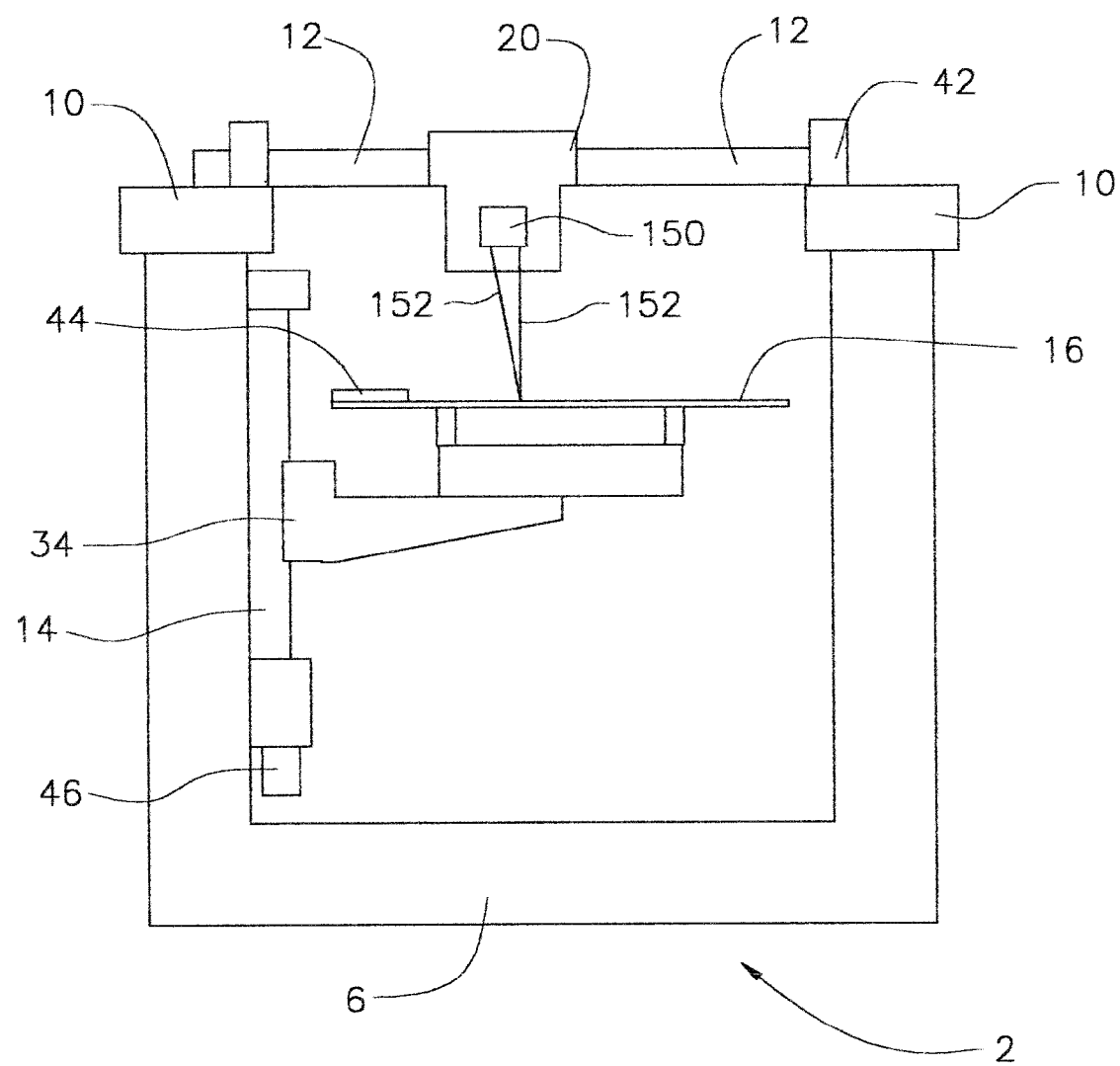
FIG. 12 is a back view of a material deposition device in accordance with the present invention showing a sensor attached to the back of the tool interface. The sensor detects properties of the substrate, of the article being fabricated, and of the materials being deposited.

Alternative embodiments for this type of non-contact geometric sensing may include confocal chromatic displacement sensor, ultrasonic range sensor, a laser triangulation sensor as illustrated in FIG. 12, which can provide superior distance resolution, and reduced sensitivity to the reflectivity of the material. Laser triangulation sensor 150 is preferably positioned on the back side of tool interface 20 and emits lasers 152 onto substrate 16. Other machine vision sensing technologies are also available, including microscopic video capture at the point of deposition.

One of the challenges of employing multiple tools in a freeform fabrication system is that of "registration," namely ensuring that the point of material deposition is accurately known by the system controller for each tool that is used. The tools have finite rigidity, and even using precision robotic tool changers to mount tools to the positioning system, there is a limit to the repeatability of the position of the point of action of the tool. Without accurate registration, material deposited by one tool will not be positioned correctly relative to material deposited by previous and subsequent tools used, and significant geometric and functional errors will result from the manufacturing process.

Figure 13:
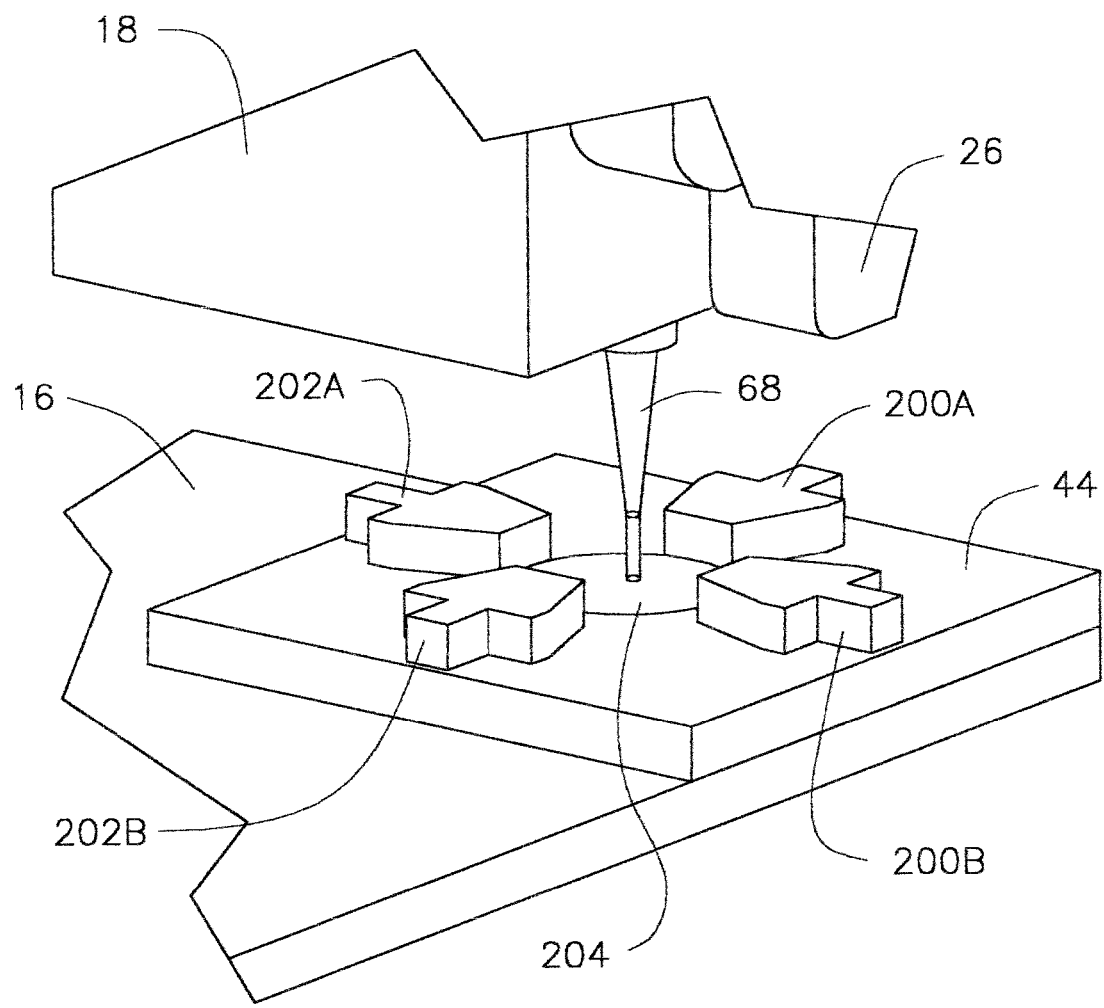
FIG. 13 is a perspective view of a tip calibration sensor positioned on a substrate of a material deposition device. The tip calibration sensor enables the system controller to be aware of the precise location of a reference point on the tool or tools attached to the tool interface relative to the tool interface.

Two approaches have been explored for calibrating the location of the point of deposition. The first, and inferior method, requires that for each time a tool is mounted for use on the positioning system, a human operator must manually control all 3 axes of the positioning system, placing the tip of the tool in contact with a "registration mark" on the build surface. The position of this mark is stable over time and at a known location within the volume accessible to the positioning system. Thus, when the point of deposition of the current tool is located at this mark, the positioning system can read the displacement between this location and the known location of the registration mark, and thereby infer the position of the point of deposition of the current tool. Because this method requires an operator to perform the calibration manually through visual alignment, and for each tool change, the labor and time required are impractical (1-5 minutes for each calibration, possibly hundreds of tool changes during a relatively simple build operation). For this reason, a second method has been developed which automates this calibration process. As illustrated in FIG. 13, calibration device 44 is mounted on substrate 16. Calibration device 44 eliminates the need for the registration mark and reliance on the human operator's eye. Calibration device 44 has two infrared emitters 200A-B and two infrared detectors 202A-B oriented orthogonally to each other, and Teflon-covered analog force sensor 204 located at the intersection of the two optical axes.

The optical emitter/detector pairs (200A-B and 202A-B, respectively) function by detectors 202A-B returning a signal level which is higher when less infrared light is received from emitters 200A-B. Thus, when an object obstructs the optical axis of an emitter/detector pair, the signal will be larger than when no object is present, and the signal varies symmetrically as an object moves perpendicularly across the optical axis. This sensing arrangement easily detects small deposition tips, such as a syringe needle 68 with an outside diameter of 0.007". The system control software monitors the analog output signals from the optical sensors, while commanding the positioning system to perform a search pattern. When tool tip 68 has been positioned at the center of both optical axes, providing the X and Y coordinates of the tool tip, the Z-axis is elevated gradually, raising the sensor assembly toward tool tip 68 until a signal is detected by force sensor 204. Force sensor 204 is designed to detect very small changes in applied force with very little displacement, so detecting contact with the sensor requires very little force be applied to tool tip 68. When a threshold force is detected, the Z coordinate of tool tip 68 is identified.

In an alternative embodiment of calibration device 44, a hole is left in the center of sensor 204, extending directly through substrate 16. An initial rough positioning of tool tip 68 will be used to maneuver tool tip 68 through the hole so that it extends below the plane of substrate 16. A compressed gas jet located beneath the substrate 16 at this location will be activated briefly to blow away any residual material attached to tool tip 68, if the tool is delicate. If tool tip 68 is less delicate and requires more vigorous cleaning, a wire brush, rubber scraper blade, or similar device will be located proximate to calibration device 44 to be used for tip cleaning (by relative motion). Tool tip 68 will then be raised upward through the hole, and the search pattern used to identify the X, Y, and Z coordinates of tool tip 68—the X and Y coordinates first as before with the current version of the sensor, and the Z coordinate by observing simultaneous rising signal edges in detectors 200A-B which is associated with tool tip 68 leaving both optical axes simultaneously in the Z-direction.

Before commencing to fabricate an article and/or after having made each deposit of material, the system can collect 3-dimensional geometry data of the current state of the substrate and any objects therein, the material deposited, and the article being fabricated. Precisely capturing the geometry of the substrate immediately prior to manufacturing, planning, and commencing deposition is important when an article is to be fabricated onto or into an object whose geometry and location are not precisely known, are not easily represented, and/or are not static, such as a living organism. This permits the manufacturing plan to be generated in a manner which accommodates the actual geometry of the substrate, preventing collision between the deposition tool and the substrate, and improving deposition quality by maintaining proper separation between tool and substrate. The more dynamic the substrate, the more frequently such data must be captured. If necessary, geometric sensing apparatus can be located very near to the orifice of a tool and data collected continuously, enabling the system controller to track the motion of the substrate and command compensatory motion of the deposition tool relative to the substrate while depositing material in order to achieve the desired deposit geometry. After having made a deposit of material, the system can collect 3-dimensional geometry data of the current state of the product being fabricated. Any substantial unexpected deviation of the deposit geometry from that predicted by the manufacturing simulation for the current manufacturing step will be captured as an error volume (polytope). This error volume will be sent back to the manufacturing planning software which may modify the manufacturing plan in order to attempt to remove the error by making additional material deposits, or may cancel the entire manufacturing operation. Any unremediated error will be incorporated into the manufacturing simulation, to improve prediction of the characteristics of the finished product. This error data may also be used to modify the materials/tools/substrates and design databases to reflect any knowledge gained from identifying the cause of the error. Other sensing devices may be used in an analogous manner to provide spatial and/or temporal monitoring of other aspects of the substrate, of the state of the material being deposited, and of the article being fabricated. Deviations of the measurements from the desired values, as simulated in the simulation module of the system software, or as expected from the data in the materials/tools/substrates database, can be used to generate compensatory actions which may be executed prior to making the next deposit of material. For instance, given a deposit of a chemically reactive material which changes color as it reacts, a machine vision sensor can detect that the color of a region of deposited material is not what is expected for this material given the data present in the materials/tools/substrates database, the time elapsed since the material was deposited, and the conditions experienced by the material as measured by sensors within the substrate module. The system can generate a compensatory action which is to apply local heating via a material modification tool to those areas which are under reacted, and to reduce the temperature in the receptacle of the substrate module in order to slow the reaction of those areas which are overreacted.

Figure 14A:
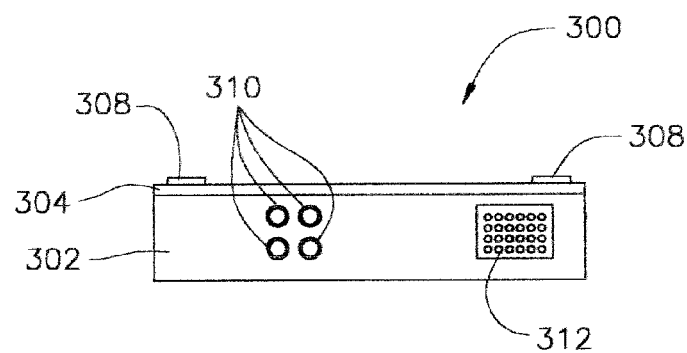
FIG. 14A is a front view of a module in accordance with the present invention which is attachable to the substrate. A plan view (FIG. 14B) and a side view (FIG. 14C) of the substrate module are also shown.
Figures 14B, 14C:
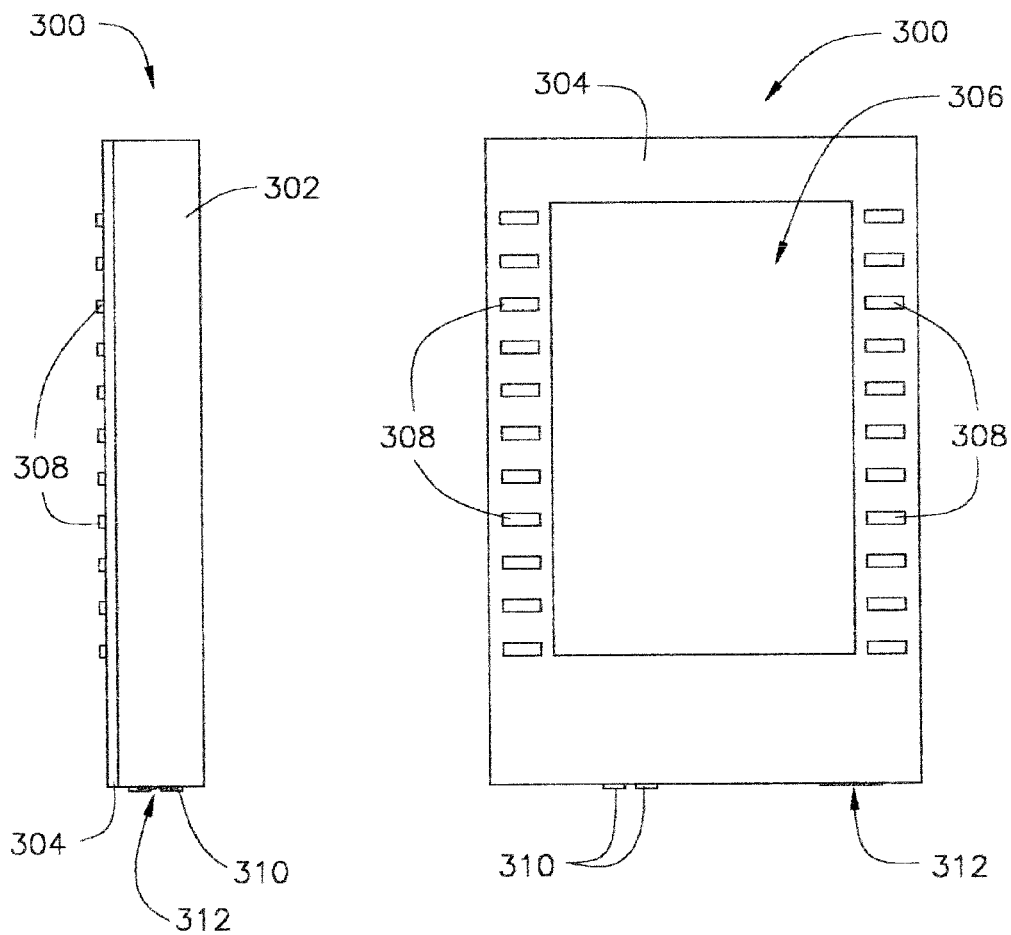

To further enable fabrication of complex articles, such as living tissues, the fabrication system of the present invention may have one or more substrate modules attachable to the substrate. FIGS. 14A-C illustrate a module of the present invention, which is attachable to the substrate. Module 300 has housing 302 and lid 304, which rests on housing 302. Module 300 is also provided with auxiliary material interfaces 310 and electrical interface 312. Material is dispensed from a material deposition tool into receptacle 306. Alignment sockets or pins are located on the base of module 300 and/or at the periphery of electrical interfaces 310 and/or auxiliary material interfaces 312 to assist in aligning of module 300 with other modules and/or with electrical and auxiliary materials interfaces of the material deposition device and/or of the tool rack or other storage system. In addition, the alignment sockets and/or the electrical interfaces and/or the auxiliary materials interfaces of module 300 may be connected to mating interfaces on a transfer system in order to minimize the amount of time that module 300 spends disconnected from utilities, materials, and communications with the rest of the article fabrication system. Fixture points 308 are positioned on lid to assist in securing and positioning foreign objects, such as sensors, exogenous devices, or living organisms within the receptacle so that material can be deposited onto or into them.

Figure 15:
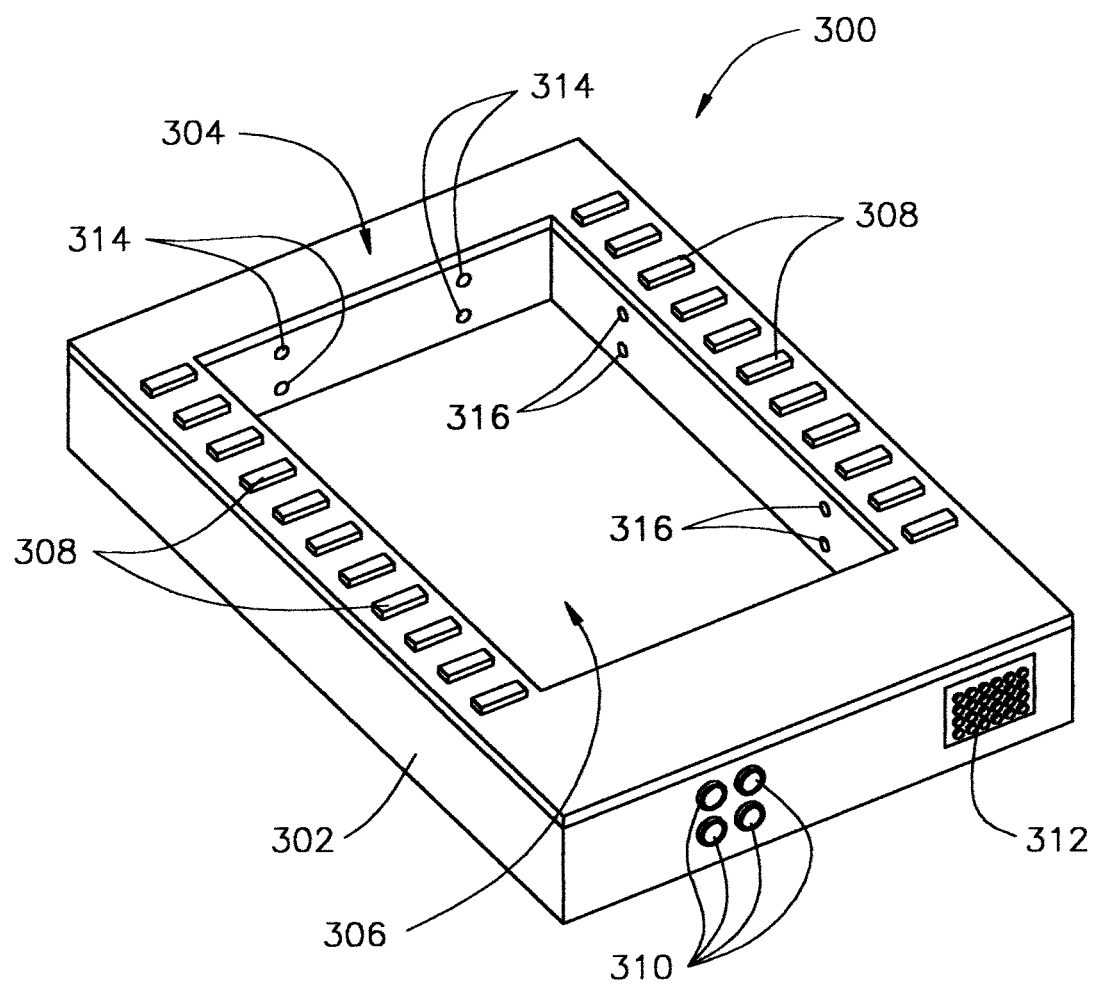
FIG. 15 is a perspective view of a module in accordance with the present invention depicting a receptacle into which material from a material deposition device is dispensed and examples of fixture points, interfaces, and sensing and actuation ports which may be included in the module.

FIG. 15 is a perspective view of module 300, which illustrates receptacle 306. Receptacle 306 is a special region of module 300 that is intended to receive material dispensed from a material deposition tool. Receptacle 306 is specialized to suit the properties and needs of the material and/or the component being fabricated. In one embodiment, receptacle 306 is a simple flat surface, a Petri dish, a foam structure, or a geometrically complementary or semi-complementary surface. Receptacle 306 may contain a liquid, gas, and/or solid, such as a crosslinking solution. To support in vivo fabrication, receptacle 306 may be or contain part or all of the body of an organism. To support this type of receptacle, module 300 may have fixture points 308 to which clamps or dissecting tools may be attached in order to hold the organism or object in a manner which assists the material dispensing process. Located inside of receptacle 306 are sensor ports 314 and auxiliary material ports 316. Sensor ports 314 enable monitoring of the conditions inside receptacle 306 before, during, and after the fabrication process (i.e. the dispensing of material into receptacle 306. Auxiliary material ports 316 are openings through which auxiliary materials enter or leave receptacle 306.

Figure 16:
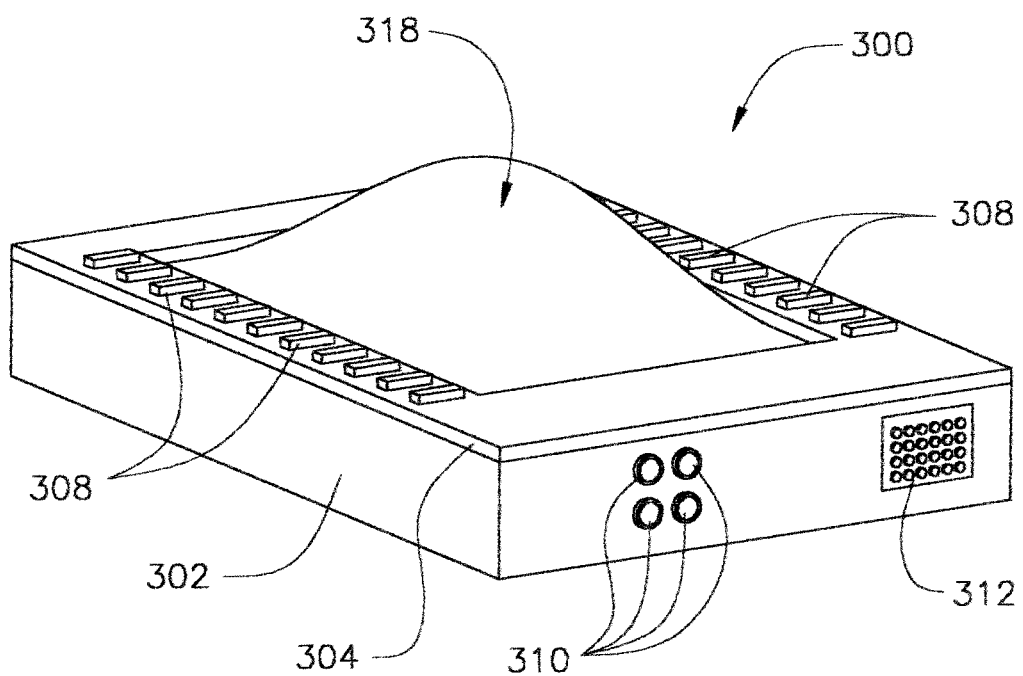
FIG. 16 is a perspective view of a module in accordance with the present invention in which a receptacle is enclosed.

In a preferred embodiment, receptacle 306 is provided with enclosure 318 illustrated in FIG. 16. Enclosure 318 provides a controlled (e.g. sterile) environment for receptacle 306. In one embodiment, enclosure 318 is a permeable barrier or boundary and material is deposited from a material deposition tool into the enclosure by piercing the enclosure. In an alternative embodiment, enclosure 318 is a non-permeable barrier or boundary. In a preferred embodiment, enclosure 318 is provided with an access port through which material dispensed from a material deposition tool may penetrate enclosure 318.

Figure 17:
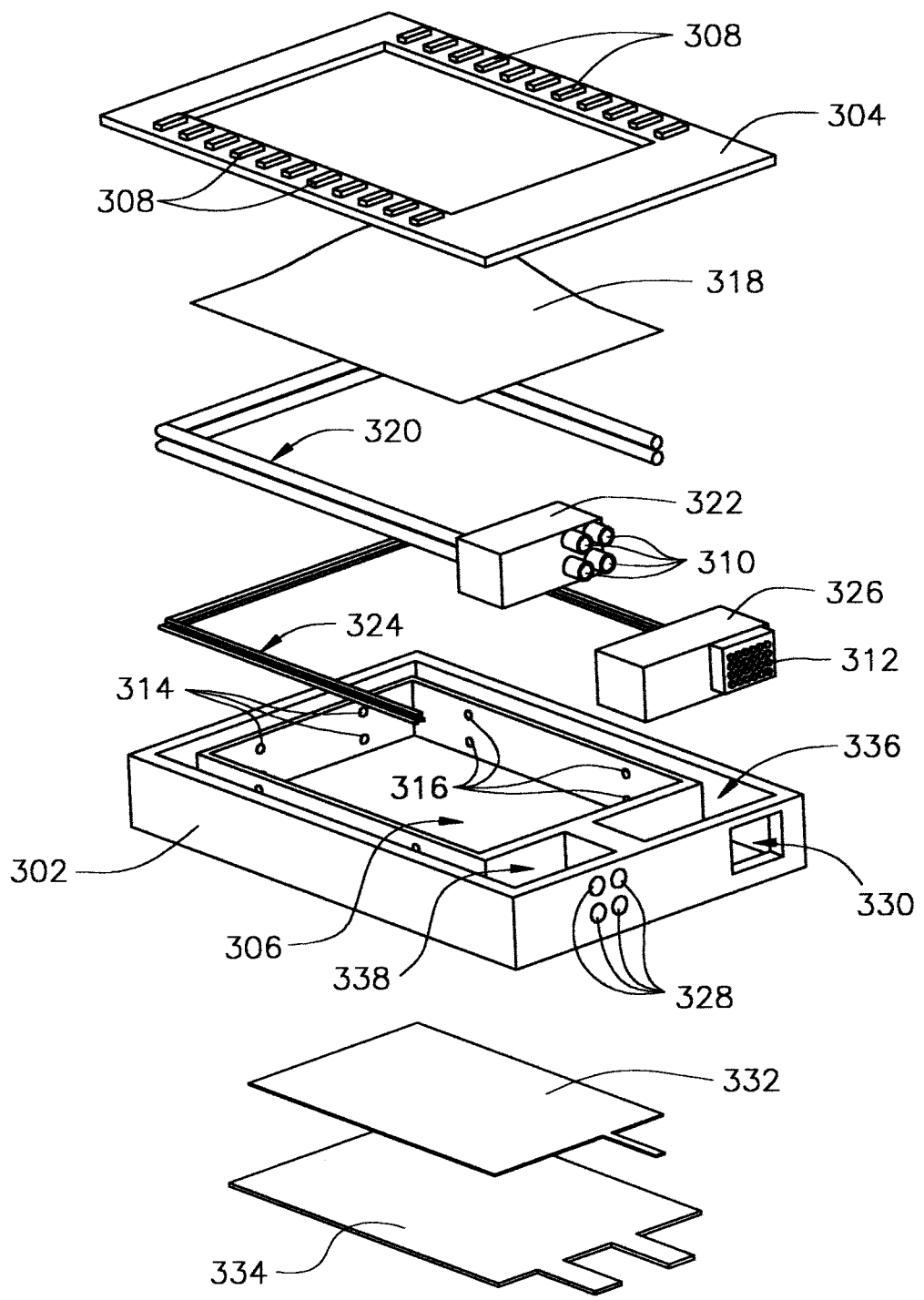
FIG. 17 is an exploded perspective view of a module in accordance with the present invention.

FIG. 17 is an exploded perspective view of module 300. Housing 302 is provided with channel 336, which houses electronics module 326 and electrical wiring 324. Port 330 allows exposure of electrical interface 312 for connection of electronics module 326 to an on-board controller or the system controller. Electrical interface 312 operably connects module 300 to the rest of the fabrication system and/or to other substrate modules. Electrical interface 312 also permits sending and/or receiving of signals (wired or wireless) and/or power. A preferred electrical interface 312 includes, without limitation, mateable electrical connectors, umbilicals, and optical or radiofrequency transceivers.

Electronics module 326 contains any signal conditioning and processing required to operate and monitor whatever sensors and actuators are in module 300. Electronics module 326 may also contain local intelligence and control, local power, and communications devices associated with monitoring/controlling, powering, and communication for module 300. The signals and power flowing between electronics module 326 and the sensors and actuators within substrate module 326 (including those that might be attached to or embedded within an organism, object, or device attached to module 300) flow through conduits such as wiring, cables, or wirelessly.

Sensing control in receptacle 306 is carried out as the environment in receptacle 306 is sensed through sensor ports 314 and communicated via electrical wiring 324 to electronics module 326. Thus, in a preferred embodiment, substrate module 300 is equipped with sensors. Sensors of module 300 monitor the state of module 300 and its contents. For example, the sensors of module 300 may be a sensor for light, temperature, fume presence, humidity, fluid presence, deposited material presence, auxiliary material flow rate, acceleration, mechanical force, electrical current, electromagnetic fields, material conductivity/resistivity, color, spectral absorptivity/reflectivity, vital signs, and/or tilt angle. Sensors may be positioned anywhere within module 300 or its contents, for instance, embedded in an organism contained within/mounted to module 300, and may be monitored via wire or wirelessly by the local intelligence and control of module 300, or directly by the system controller.

Channel 338 houses auxiliary materials control module 322 and auxiliary materials tubing 320. Electrical control and sensing signals and electrical utilities required by the auxiliary materials control module 322 may be supplied via connection of auxiliary materials control module 322 to electronics module 326 via wiring routed internally to module 300, running directly from channel 338 to channel 336. These signals may also be routed via electronics interface 312 in order to permit them to be connected thereby to the system controller, to the electronics modules 326 and auxiliary materials control modules 322 of other substrate modules 300, substrate 16 of the material deposition device, and/or to module storage and/or transfer devices.

Auxiliary control of receptacle 306 is carried out as auxiliary materials are distributed and/or collected throughout module 300, including to and/or from devices or organisms positioned in receptacle 306, via auxiliary material ports 316 and auxiliary conduits 320 which, in a preferred embodiment, are pipes, channels, or tubing. Auxiliary material control module 322 contains mechanisms, sensors, or actuators directly associated with sensing and control of the auxiliary materials. These may, in turn, be connected to electronics module 326, or may be interfaced directly to the system controller (e.g. through electronics interface 312). Auxiliary material control module 322 may contain valves, flow sensors, mixing devices, regulators, and/or vibrators.

Auxiliary material interfaces 310 send or receive auxiliary material including, without limitation, solids, fluids, and/or gases to and/or from receptacle 306 via auxiliary material ports 316. Auxiliary material interfaces 310 may mate with auxiliary material interfaces of other parts of the fabrication system, including other substrate modules, substrate module storage (e.g. a tool rack), transport devices, or substrate 16 of the material deposition device. For example, auxiliary material interfaces 310 could provide module 300 with cell culture media or other nutrients, pressurized fluids for power, gas supplies for atmospheric control, heated or cooled fluids for heat exchange, and/or clear module 300 (i.e. receptacle 306) of waste material.

In a preferred embodiment, module 300 is also equipped with actuators, which change and/or maintain the state of module 300 (i.e., receptacle 306) and its contents. Actuators may be located anywhere within module 300 or its contents, and may be controlled via wire or wirelessly by the local intelligence and control of module 300, or directly by the system controller. For example, actuators may provide active supply or suppression of light, UV light, vibration, ultrasound, heat, humidity, contaminants, mechanical forces, mixing, electromagnetic fields, or gas mixtures. Other examples of auxiliary control include fluid pumping or flow regulation, receptacle tilting, and/or auxiliary material pumping or flow regulation. These operations may include controlling the state of a living organism or a complex device attached to or contained within the receptacle—for instance providing intravenous materials, or mechanical or electrical stimuli. This can be useful in the fabrication and development of tissues which require external stimuli for proper formation, such as bone, or in the continual operation of complex devices, such as sensor arrays or micropumps, whose state can be controlled even as material is being deposited on and around them.

The local intelligence and control of module 300, which may reside in electronics module 326 of module 300, preferably controls the aforementioned actuators and sensors of module 300 alone or in cooperation and communication with the system controller. It may perform this sensing and control based upon its own program, or in concert with the manufacturing plan which resides in the software of the system controller. The local intelligence and control of module 300 may also log data such as the commands given to actuators or feedback from sensors.

The local power of module 300 provides power to module 300 in the case that module 300 is not supplied with external power. Local power may be included within electronics module 326. In a preferred embodiment, the local power includes, without limitation, batteries, capacitors, fuel cells, and/or photovoltaic cells. Local power, for example, enables module 300 to continuously log data, sense and control its own state, and the state of its contents, even when disconnected from the rest of the fabrication system.

Module 300 may also have heating/cooling element 332 to provide temperature control of receptacle 306.

Lid 304 and bottom lid 334 contain substrate module 300.

Figure 18:
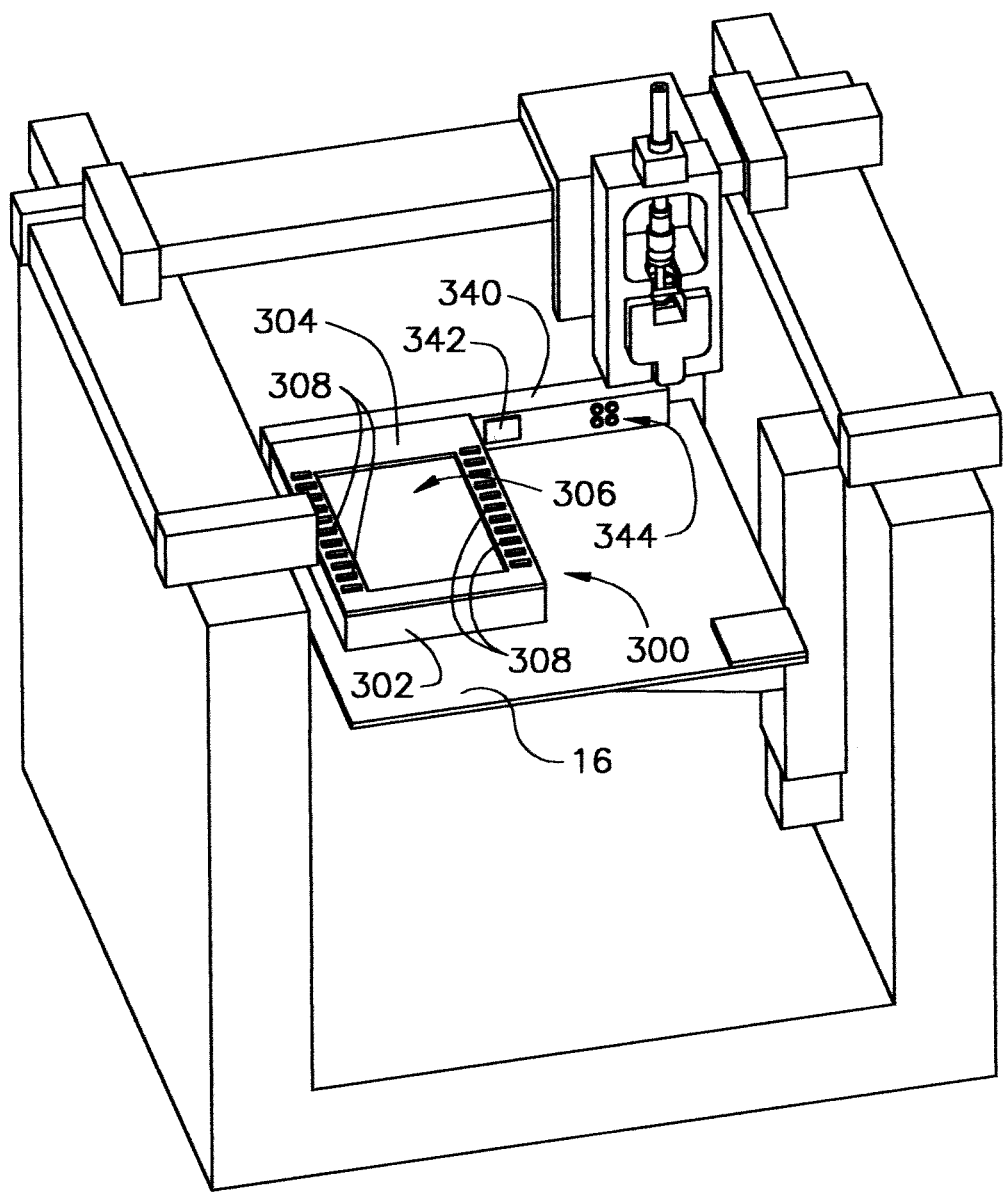
FIG. 18 is a perspective view of a fabrication system in accordance with the present invention in which a module is attached to a substrate.
Figure 19:
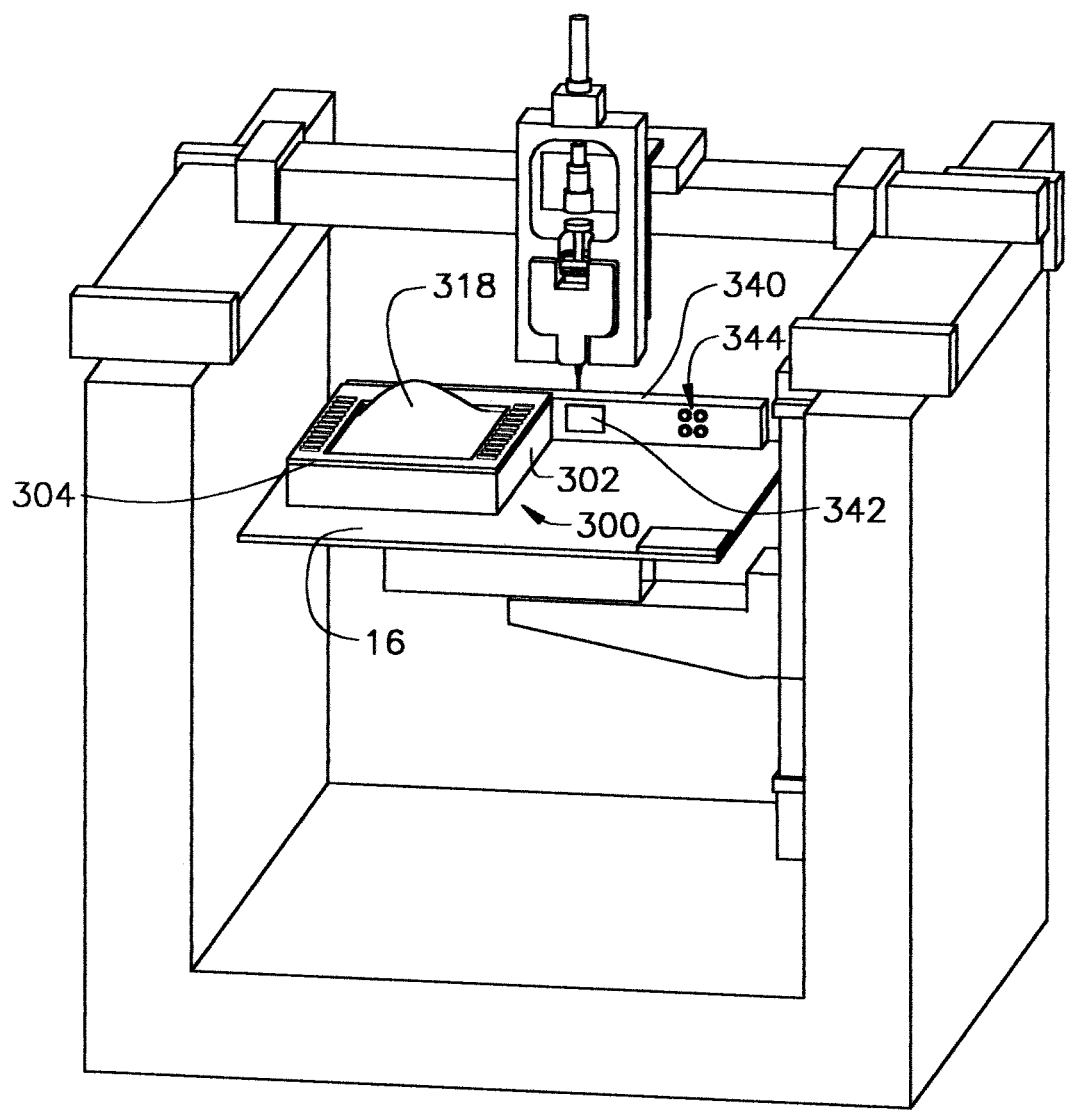
FIG. 19 is a perspective view of a fabrication system in accordance with the present invention in which a module having an enclosed receptacle is attached to a substrate.

As shown in FIG. 18, module 300 is attachable to substrate 16 of the material deposition device of the present invention. Mechanical attachment of module 300 to substrate 16 may, for example, be carried out through one or more of the following means: alignment pins or sockets, bolts, vacuum chuck mating surfaces, rails, and/or magnets, adhesives, or inter-surface friction. In a preferred embodiment, module 300 attaches to module interface bar 340 positioned on substrate 16. Module interface bar 340 is preferably equipped with one or more docking stations, each docking station having electronic interface 342 connectable to electrical interface 312 and auxiliary material interface 344 connectable to auxiliary materials interface 310. Together, these mechanical, electrical, and auxiliary materials attachments allow the precise and repeatable positioning, electrical communication and utilities supply, and auxiliary materials supply and return of one or more units of module 300 during the time in which module 300 resides atop substrate 16 during the course of article fabrication. In FIG. 19, module 300, which is equipped with enclosure 318, is attached to substrate 16.

In a preferred embodiment, module 300 is disposable or contains disposable components, for instance to improve sterility.

Module 300 may be manually or automatically transported to/from the material deposition device. In a preferred embodiment, module 300 is transported by the transfer device of the system of the present invention.

When employed in the fabrication system of the present invention, module 300 serves the purpose of receiving the dispensed material in a fashion that supports the objective of the fabrication. Module 300 provides a local environment for the dispensing region and a surface that is suitable for fabrication. Module 300 may monitor and/or control, alone or in concert with the system controller, a variety of sensors and actuators which interact with the contents of the substrate module. In a preferred embodiment, module 300 has a local intelligence and control and/or local power. Alternatively, module 300 is operably connected to the system controller. Module 300 may be connected to and/or in communication with the system controller before, during, and/or after a fabrication process, for instance to allow monitoring and control of module 300 and its contents to be an integral part of a manufacturing plan executed by the system controller.

Suitable deposition materials for use in the system of the present invention include, without limitation, any material capable of being deposited from a material deposition tool onto the substrate. The type of material preferred will depend on the type of material deposition tool being employed. For example, when a fusible-material extrusion tool is employed, suitable materials include, without limitation, thermally liquefied plastics, low melting-point metals, and other fusible materials. When a syringe cartridge is employed, suitable materials include, without limitation, virtually any liquid, slurry, or gel.

Using a given material with a solid freeform fabrication system typically requires modifying that material somewhat to make it useable by one of the tools within the system, or at an extreme, development of an entirely new tool. If it is desired that the new material should be able to be incorporated into designs made with a variety of materials, then a significant amount of effort is required to ensure compatibility of materials and processes, to develop operating parameters for tools, and to fully characterize the resulting materials, deposits, and generate all of the data required to enable the system to make full use of the material. For this reason, each successful material formulation is a significant achievement in itself. Several such formulations have been developed, including tissue engineering materials, zinc-air battery materials, polymer actuator "artificial muscle" materials, and others.

Methods such as molecular self-assembly can be combined with this system permitting localized self-assembly of molecular level structures. Ink-like materials can be made which are MEMS devices dispersed in a liquid carrier. The MEMS devices can be deposited as a normal ink. After evaporation of the carrier, the devices can be electrically connected by depositing electrically conducting materials in appropriate patterns.

Novel applications of this system in the areas of biomedical implants can include controlling the biocompatibility of conventionally manufactured biomedical implants by depositing compatible living tissues, or appropriate chemicals, as a covering for the devices. Novel biomedical implants can be produced which are hybrids of freeform fabricated materials— both biological and non-biological—with conventionally manufactured devices which are embedded within. This can result in implants which have functionality that is unachievable by conventional manufacturing means.

For most purposes, the system should be enclosed. The enclosure primarily serves two purposes: safety and manufacturing environment control. The enclosure includes fume extraction filtration and/or ducting connections to external ventilation in order to allow use of the system in a human occupied space. The enclosure also prevents human operators from contact with high temperatures, high voltages, laser radiation, etc.

The enclosure also permits the system to control the ambient environment in which fabrication takes place. Temperature, humidity, and gas mix of the environment, as well as illumination can all be controlled over time. This permits the system to control the evolution of the properties of deposited materials over time. For instance, the system can maintain a low temperature to limit chemical reaction until all of a certain material has been deposited, then cause reaction in the deposited material by elevating the temperature, or viability of living tissues being deposited can be enhanced by maintaining incubating conditions.

For certain purposes, especially when working with very sensitive materials, or under very stringent sterility conditions, it may be desirable to include a "local enclosure" around the object being fabricated. This can take the form of a sterile and/or sterilizable membrane or bag which encloses the active region of the substrate, and which can be penetrated by the tip of a tool in a selective fashion. This arrangement permits the upper surface of the membrane to move with the tool while the lower surface remains stationary relative to the build surface and the object being fabricated. Such local enclosures can, for instance, permit use of a version of the fabrication system not specifically designed for sterile work to work with materials which require high standards of sterility, further enhancing the breadth of utility of the system for exploring freeform fabrication with novel materials without extensive specialized modifications specifically for those materials.

Systems of the present invention may be used in the fabrication of a variety of articles including, without limitation, the fabrication of food products. For example, a system of the present invention is suitable as a household product for production of breads, pastries, cakes, candies, or other food items. Such food items could be constructed using systems of the present invention to produce food articles with various 3D shapes and internal structures (e.g., a pattern that reveals an inscription when a slice is taken, or in various 2D or 3D shapes downloaded from the internet). When fabrication systems in accordance with the present invention are employed in the production of food items, material deposition tools of the present invention may include, without limitation, food processing devices and substrates may include, without limitation, modules suitable for baking and/or cooking.

Another aspect of the present invention relates to a method of fabricating an article. This method involves providing the above-described article fabrication system. Material is dispensed from the material deposition tools, when mounted on the tool interface of the material deposition device, in amounts and at positions on the substrate in response to instructions from the system controller, whereby an article is fabricated on the substrate.

In a preferred embodiment, the article fabricated by the method of the present invention is a living tissue.

A preferred material according to the method of the present invention is a material having seeded cells, preferably a hydrogel having seeded cells. Suitable hydrogels include, without limitation, alginate, agarose, collagen, chitosan, fibrin, hyaluronic acid, carrageenan, polyethylene oxide, polypropylene oxide, polyethylene oxide-co-polypropylene oxide, hydroxypropyl methyl cellulose, poly(propylene fumarate-co-ethylene glycol), poly(ethylene glycol)-co-poly (lactic acid), poly(vinyl alcohol), KDL12 oligopeptides, and poly(n-isopropyl acrylamide).

The hydrogels preferably have a controlled rate of crosslinking through the adjustment of environmental variables including, but not limited to, temperature, pH, ionic strength, heat, light, or the addition of chemical crosslinking agents such as calcium, magnesium, barium, chondroitin, sulfate, and thrombin. The cross-linking compound is preferably provided in a weight ratio of hydrogel to cross-linking compound of about 1:100 to 100:1, respectively. In a more preferred embodiment, the weight ratio of cross-linking compound to hydrogel is about 1:5.3. In an even more preferred embodiment, the cross-linking compound is calcium sulfate.

In one embodiment, cells in the hydrogel are of a single cell type. Suitable cell types include, without limitation, all mammalian or plant cells. Preferred cell types include, without limitation, chondrocytes, osteoblasts, osteoclasts, osteocytes, fibroblasts, hepatocytes, skeletal myoblasts, cardiac myocytes, epithelial cells, endothelial cells, keratinocytes, neurons, Schwann cells, oligodendrocytes, astrocytes, pneumocytes, adipocytes, smooth muscle cells, T cells, B cells, marrow-derived stem cells, hematopeotic stem cells, osteoprogenitor cells, neural stem cells, and embryonic stem cells. Alternatively, cells in the hydrogel may be of more than one cell type.

Dispensing material from the material deposition tools, according to the method of the present invention, is preferably carried out under sterile conditions. In one embodiment, dispensing of the material may be carried out in a hermetically sealed envelope.

The method of fabricating a living tissue may further involve determining geometry and cell distribution of the article prior to carrying out the dispensing step. The system controller may also be programmed with instructions effective to cause the dispensing steps to be carried out to produce an article with a desired geometry and cell distribution.

In one embodiment, the determined geometry is free-form. In an alternative embodiment, the geometry is an anatomic shape, preferably patient-specific.

To determine geometry, a computerized scan of a tissue/organ may be generated, such as a scan of a tissue/organ to be replaced. The geometry to be dispensed can be determined from any method capable of generating 2D and/or 3D data sets, including, without limitation, 3D laser scanning, confocal microscopy, multi-photon microscopy, computerized tomography, magnetic resonance imaging, ultrasound, and angiography.

After a hydrogel with seeded cells is fabricated pursuant to the methods of the invention, the article may be incubated under conditions effective to grow the cells. Incubation may be carried out on the substrate, or the article may be transferred to a new substrate for more optimal growth conditions.

A further aspect of the present invention relates to a method of fabricating a living three-dimensional structure. This method involves providing a data set representing a living three-dimensional structure to be fabricated. One or more compositions including a composition having a hydrogel with seeded cells is provided. The one or more compositions are dispensed in a pattern in accordance with the data set suitable to fabricate the living three-dimensional structure.

Suitable compositions for carrying out this method include hydrogels, with or without seeded cells, which in a preferred embodiment, contain cross-linking compounds to provide structure to the fabricated tissue.

EXAMPLES

The examples below are intended to exemplify the practice of the present invention but are by no means intended to limit the scope thereof.

Example 1

Direct Freeform Fabrication of Living Pre-Cell-Seeded Alginate Hydrogel Implants in Anatomic Shapes Articular chondrocytes were isolated from cartilage from the femeropatellar groove of 1-2 week old calves by collagenase digestion (Genes et al., "Effect of Substrate Mechanics on Chondrocyte Adhesion to Modified Alginate Surfaces," *Arch. Biochem. Biophys.* 422:161-167 (2004), which is hereby incorporated by reference in its entirety). Chondrocytes were suspended in 2% ultrapure low viscosity alginate in phenobarbital sodium ("PBS") at a concentration of 50 million cells/mL. The suspension was vortexed and mixed with 10 mg/mL $CaSO_4$ in PBS in a 2:1 ratio. The gel was placed in a sterile 10 mL syringe with a 22 gauge SafetyLok tapered syringe tip and loaded into a gel deposition tool.

In parallel, a computerized tomography ("CT") scan of an ovine meniscus was converted into a stereolithography file using Microview software. The file was then imported into a custom software package and was used to plan tool paths for the gantry robot. The gantry robot moved the gel deposition tool in prescribed tool paths and fabricated the implant in a layer-wise fashion. After printing, the implant was soaked in a 20 mg/mL $CaCl_2$ solution in PBS for 30 minutes to further cross-link the gel. Finally, the gel was transferred to Dulbecco's minimal essential medium ("DMEM") growth media with 10% fetal bovine serum.

The viability test was performed with a live/dead viability assay using 0.15 µM calcein AM and 2 µM ethidium homodimer-1 (EthD-1) and a staining time of 35 minutes at room temperature. Samples were analyzed in a Bright Line counting chamber using a Nikon TE2000-S microscope equipped with an epifluorescence attachment and a Spot RT digital camera.

The sterility test was performed by culturing a printed sample in growth media without antibiotics for 8 days. Bacterial presence was tested for in the cultured sample with 100 µM BacLight Green bacterial stain a Bright Line counting chamber, and a Nikon TE2000-S microscope equipped with an epiflourescence attachment and a digital camera.

The technique used to mix the alginate and crosslinker has a strong effect on the physical properties of the gel (Hung et al., "Anatomically Shaped Osteochondral Constructs for Articular Cartilage Repair," *J. Biomech.* 36:1853-1864 (2003), which is hereby incorporated by reference in its entirety). The mixing technique that yielded a "printable" gel involved 10 full-cycle pumps between two 10 mL syringes through a stopcock over a total of 10 seconds.

Viability tests successfully detected both live (FIG. 20A) and dead (FIG. 20B) cells in printed gels. Based on this data the viability of the printing process was determined to be 94±5% (n=15). After 8 days of incubating a printed gel sample without any antibiotics in growth media, less than 1 bacterium per 0.9 µL was detected (n=12).

Using a CT scan of bovine meniscus, an STL file was generated (FIG. 21A) and used to plan the robot's tool paths.

The printed meniscus-shaped gel (FIG. 21B) had a geometric resolution of 0.4 mm. The total printing time, from when the deposition tool was loaded with gel to the end of the print-job, was less than 6 minutes.

This research demonstrated the use of an open-architecture robotic printing platform to successfully 3-D print infection-free, living, preseeded hydrogel implants of anatomic geometries. One of the greatest challenges was changing the formulation of a moldable hydrogel into one that is "printable." Formulation concentrations were adjusted to set a crosslinking rate that was fast enough for the deposited gel to hold its shape yet slow enough to prevent material shearing upon deposition. Other tissue engineering technologies such as injection molding (Chang et al., "Injection Molding of Chondrocyte/Alginate Constructs in the Shape of Facial Implants," *J. Biomed. Mat. Res.* 55:503-511 (2001), which is hereby incorporated by reference in its entirety) or casting (Hung et al., "Anatomically Shaped Osteochondral Constructs for Articular Cartilage Repair," *J. Biomech.* 36:1853-1864 (2003), which is hereby incorporated by reference in its entirety) have the potential to produce anatomically shaped implants. However, these require the use of negative templates which may be difficult or impossible to produce in extremely complex geometries. Further, the elimination of the mold decreases the time necessary for implant production. An additional advantage of this technology is that the system has been designed to handle multiple-material print jobs (Malone et al., "Freeform Fabrication of 3D Zinc-Air Batteries and Functional Electro-Mechanical Assemblies," *Rapid Prototyping Journal* 10:58-69 (2004), which is hereby incorporated by reference in its entirety). This capability to print gel implants of multiple types of gel enables the fabrication of implants with spatial heterogeneities distributed in prescribed positions with a geometric resolution of 0.4 mm. The ability to rapidly fabricate implants with spatial heterogeneities in cell-type or concentration would be a great advantage in producing tissues such as articular cartilage, meniscus, or intervertebral discs that contain multiple cell types of distinct distributions.

Example 2

Direct Freeform Fabrication of Spatially Heterogeneous Living Cell-Impregnated Implants Robotic Test Platform An open-architecture gantry robot has been designed and used in this research (Malone et al., "Freeform Fabrication of 3D Zinc-air Batteries and Functional Electro-mechanical Assemblies," *Rapid Prototyping Journal* 10:58-69 (2004), which is hereby incorporated by reference in its entirety). The tool paths are generated by path planning software, which takes multiple stereo lithography files corresponding to multiple material types as input. This system has been designed to allow the printing of multiple materials within a single part. This capability is used to print multiple gels with varying cell types, chemical concentrations, cell densities, etc. The robot is capable of moving the deposition tool to a specified position with accuracy and repeatability of ±25 μm. The full specifications of this robotic system are given in Table 1.

TABLE 1

Fabrication System Performance Specifications

| | | | |
|---|---|---|---|
| Minimum material stream/drop diameter | 250 μm | 0.010M. | |
| Materials cross-section area | $4.9 \times 10^{-8}$ m$^2$ | | |
| Build rate | $2.5 \times 10^{-9}$ m$^3$/s | 0.55 in.$^{-3}$/h | |

TABLE 1-continued

Fabrication System Performance Specifications

| | | |
|---|---|---|
| Nominal speed along path | 0.05 m/s | |
| Min.-turn radius at nominal speed | 125 μm | $4.92 \times 10^{-3}$ in |
| Tool position accuracy (±) | 25 μm | $9.84 \times 10^{-4}$ in |
| Tool position repeatability (±) | 25 μm | $9.84 \times 10^{-4}$ in |
| Positioning resolution | 5 μm | $1.97 \times 10^{-4}$ in. |
| Build envelope x | 0.3 m | 11.8 in. |
| Build envelope y | 0.3 m | 11.8 in. |
| Build envelope z | 0.3 m | 11.8 in. |
| Max. XY acceleration | 20.75 m/s$^2$ | 2.12 g |

Gel Deposition Tool

The gel deposition tool must accurately deposit gels while maintaining sterility. Additionally, the tool has to enable efficient material changing. Efficient swapping of sterile materials is important for printing implants of multiple gels (each with different cell types, concentrations, etc.).

Through experimentation, it was found that elastic materials are difficult to deposit with pneumatic dispensing systems and instead a volumetrically controlled dispensing system was chosen. An ABS plastic rapid prototyped frame connects a linear actuator to the syringe cartridge. Medical-quality sterile syringes are used as the disposable material cartridges of the deposition tool. Luer lock syringes were selected in order to enable a wide variety of syringe tips to be utilized. Tool performance specification can be found in Table 2.

TABLE 2

Deposition Tool Performance Specifications

| | |
|---|---|
| Maximum applied pressure | 1592 kPa |
| Cartridge volume | 10 mL |
| Maximum volumetric flow rate | 10.5 mL/s |
| Deposition accuracy | 0.000426 mL |
| Deposition precision | 0.000426 mL |

Sterile Printing Envelope

Sterile printing conditions are a paramount concern, the lack of which would allow the printed implants to become infected. Although, as described above, a solution was found for keeping the material sterile during deposition, a way of keeping the immediate environment sterile still needed to be found.

One possible solution to this challenge was to build a sterile, hermetically sealed envelope around the immediate printing zone. While a full envelope that encompassed the printer was considered, an even smaller envelope that surrounds only the printed piece was more desirable.

Figure 22:
FIG. 22 is a photograph of a 1-millimeter thick, autoclavable, clear plastic bag used to enclose the substrate in a sterile environment.
Figure 23:
FIG. 23 is a photograph of a plastic bag containing a printed sample which has been transferred to a sterilized hood for removal of a fabricated article.

A one mm thick, autoclavable, clear plastic bag was chosen as the envelope. This bag could be loaded with a Pyrex Petri dish, sealed, and then autoclaved to ensure that the entire inside of the bag, including the Petri dish, was sterile. At this point, the inside of the bag served as a closed, sterile environment (FIG. 22). At the time of printing, the tip of the syringe and a section of the outside surface of the bag were swabbed with 70% ethanol solution and then the syringe tip was inserted through the bag. All deposited material was printed onto the sterilized Petri dish and surrounded by the previously autoclaved environment. After printing, the bag was taken to a sterile work hood where the outside of the bag was sprayed with alcohol and the sample was removed (FIG. 23). The disposable autoclave bag could then be discarded and a new bag used for the next print.

Printable Gel Formulation

The gel was composed of two components: a solution of alginate and a calcium cross-linker solution. Even though there were only two components, there were many experimental variables and it was a challenge to find a gel that was both supportive of cellular life and "printable."

Formulation Constraints

The alginate gel had to be both suitable from biological and SFF standpoints. In order for a gel to be considered biologically suitable, the alginate gel had to sustain cellular life.

In order to satisfy the SFF needs, the gel had to be "printable." By "printable," it is meant that the gel would (i) bond between layers, (ii) hold its shape against gravity, and (iii) cross-link slowly enough to prevent cell and material shearing during printing.

Formulation Process

The first step was the identification of experimental parameters. These parameters were identified as: (i) the type of cross-linker, (ii) the cross-linker concentration, (iii) the molecular weight of the alginate (iv) the mannuronic acid to guluronic acid ratio of the alginate, (v) the concentration of the alginate, (vi), how long to mix the alginate and cross-linker together and with what force (vii), how long to let the gel cross-link before printing, (viii) the choice of additives, and (ix) the range of syringe tip diameters that can be used to print the gel.

Since two separate sets of needs—biological and SFF—had to be satisfied by some single combination of the above nine parameters, each parameter's effect on the biological and SFF qualities of the materials had to be analyzed.

Biological Formulation Needs

From prior publications (Xu et al., "Injectable Tissue-engineered Cartilage with Different Chondrocyte Sources," Plast. Reconstr. Surg. 113:5 (2004), which is hereby incorporated by reference in its entirety), it was thought that the gel would be viable, i.e., support cellular life, as long as the alginate concentration was 2% in phosphate-buffered saline ("PBS") and the cross-linker concentration was less than or equal to 2% in PBS. A standard seeding density of 50 million cells per milliliter of gel was also used. These established standards served to constrain two parameters, hence they simplified the formulation process by eliminating two variables.

SFF Formulation Needs

While the biological needs were satisfied by the aforementioned published standards, the SFF-related needs had yet to be satisfied. Extensive experimentation ensued in order to determine what effects the nine experimental parameters had on the three SFF-related material properties: (i) bonding between layers, (ii) resistance to weight induced deformation, and (iii) prevention of shearing due to rapid cross-linking.

Inter-Layer Bonding Experiments

To study the effects of the nine parameters on the first SFF-related need (namely, bonding between layers), it was determined that this behavior was directly related to the rate and amount of cross-linking at the time of printing. Gels that cross-linked more quickly would be further cross-linked at the time of deposition and would be less receptive to subsequent layers because the bonds were already formed before the following layers could be deposited. Experiments were run in which the experimental parameters were varied and the cross-linking rate was given a relative, qualitative measure depending on how quickly the gel stiffened. The relationships between the experimental parameters and the ability of the gel to bond between layers are summarized in Table 3. The goal of this experiment was to find some combination of the nine parameters that yielded a gel which cross-linked as quickly as possible, yet still bonded between layers.

TABLE 3

Relationship Between Parameters and Successful Interlayer Bonding

| Experimental Parameter | Relationship with Successful Bonding Between Layers |
| --- | --- |
| Increased alginate molecular weight | (−) |
| Increased cross-linker concentration | (−) |
| Longer mixing time | (−) |
| Longer sitting time before printing | (−) |
| Larger tip diameter | (+) |

Resistance to Weight Induced Deformation Experiments

In order to see what effect each parameter had on the second SFF-related need (namely, resistance to weight deformation), each parameter's effect on the gel viscosity was studied using an automatic viscometer. It was initially thought that the viscosity would be an accurate indication of how well the gel would hold its shape against gravity. In order to further vary the viscosity, dextrose was used as a bulking agent. However, after comparing the results of the viscosity experiments to simulated prints in which the gel was layered by hand, it was clear that viscosity was not an accurate indicator of a gel's resistance to weight-induced deformation. The notion was rejected and this part of the formulation process was iterated. At this point, it was noticed that the resistance was strongly related to cross-linking rate. While a high viscosity did not help the gel hold its shape, partial cross-linking did. Therefore, the faster a gel cross-linked the better it would be able to hold its own weight. At this point, it was realized that two SFF-related needs were directly determined by cross-linking rate, that is, the bonding between layers and the resistance to gravity. However, these two needs were opposed to each other. A higher cross-linking rate would help the gel hold its shape against gravity, while at the same time it would make the layers less likely to bond with each other. Some acceptable compromise needed to be reached. The relationship between parameters and resistance to weight-induced deformation is summarized in Table 4.

TABLE 4

Relationship Between Parameters and Resistance to Weight-Induced Deformation

| Experimental Parameter | Relationship with Resistance to Weight-Induced Deformation |
| --- | --- |
| Increased alginate molecular weight | (+) |
| Increased cross-linker concentration | (+) |
| Longer mixing time | (+) |
| Longer sitting time before printing | (+) |
| Larger tip diameter | (+) |

Cross-Linking Rate Experiments

The third SFF-related need (namely, prevention of material shearing due to rapid cross-linking) was also directly related to cross-linking rate. If the material cross-linked too quickly, then the gel would significantly bond before being deposited and the bonds would be sheared upon passing through the constricted syringe tip. A summary of the relationship between cross-linking rates and the SFF-related needs can be found in Table 5.

TABLE 5

Effect of Cross-linking Rate on SFF Needs

| SFF-Related Need | High Cross-linking Rate | Low Cross-linking Rate |
| --- | --- | --- |
| Bonding Between Layers | Layers will not bond with each other (−) | Layers will bond with each other (+) |
| Resistance to Gravity | Gel can hold shape (+) | Gel cannot hold shape (−) |
| Prevention of Shearing | Gel will shear and lose mechanical properties (−) | Gel will not shear (+) |

Manual Test Prints

In order to find a cross-linker type/concentration that was suitable for the three SFF formulation constraints, various chemical combinations were tested manually. An efficient and simple test that indicates a particular formulation's printability is a conical stacking experiment. One half inch to one inch cones are deposited manually over a time range from t=0 to t=20 minutes. Each stack's ability to hold its shape against gravity is observed. Since the material properties are time dependent, testing over a large time period is important. Not only are qualitative traits noted for each formulation, but also an optimal time frame for each formulation is identified. In this optimal time frame, the properties are suitable for printing. With some formulations, the optimal time frame begins at t=0, but with others the optimal time window begins after a delay. The goal was to find a printable formulation with longest optimal time window.

Selected Formulation

The formulation used in the experiments reported herein is 2% protanal alginate (a high M-group alginate) in PBS and 0.5% calcium sulfate in PBS. The two solutions were mixed with each other in a 2:1 alginate to $CaSO_4$ ratio. Since the mixing technique greatly affects the resulting gel due to shear effects, it is important to mix the gel consistently. The mixing technique that was used was to take one 10 mL Luer lock syringe with alginate, another with cross-linker and mix the two back-and-forth through a Luer lock stopcock. A successful mixing procedure was 10 full-cycle pumps at a rate of 1 pump per second. In consideration of resolution and shearing constraints, a 0.030" diameter syringe tip was chosen.

Unseeded Gel Printing Test

This experiment verified the ability of this system to print gels of complex arbitrary geometries. In this experiment, various geometries were printed on the gantry robot in full-scale, non-sterile printing runs. The "proof of concept test pieces" illustrated in (FIGS. 24A-L) were chosen because they each demonstrate the unique capabilities of this technology and because they have interesting medical applications.

Viability of Seeded/Printed Gel Test

Figure 25A:
FIG. 25A-B are photographs of microscope views during viability tests using fluorescence microscopy filtered to illuminate living cells (FIG. 25A) and filtered to illuminate dead cells (FIG. 25B).
Figure 25B:
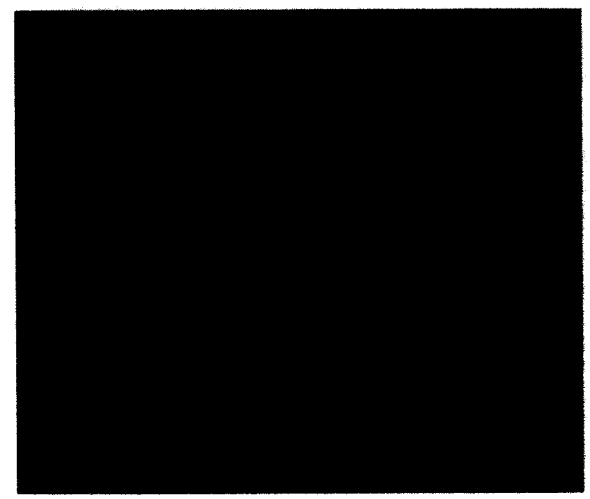
Figure 26B:
FIG. 26B is a photograph of a fabricated article produced by a fabrication system in accordance with the present invention.
Figure 26A:
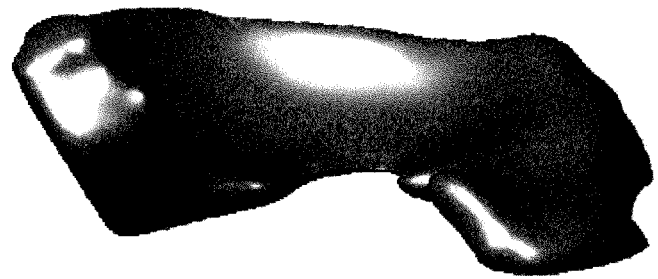
FIG. 26A is a CAD model image generated from a CT scan of a meniscus-shaped piece of cartilage used in fabricating the article shown in FIG. 26B.
Figure 27B:
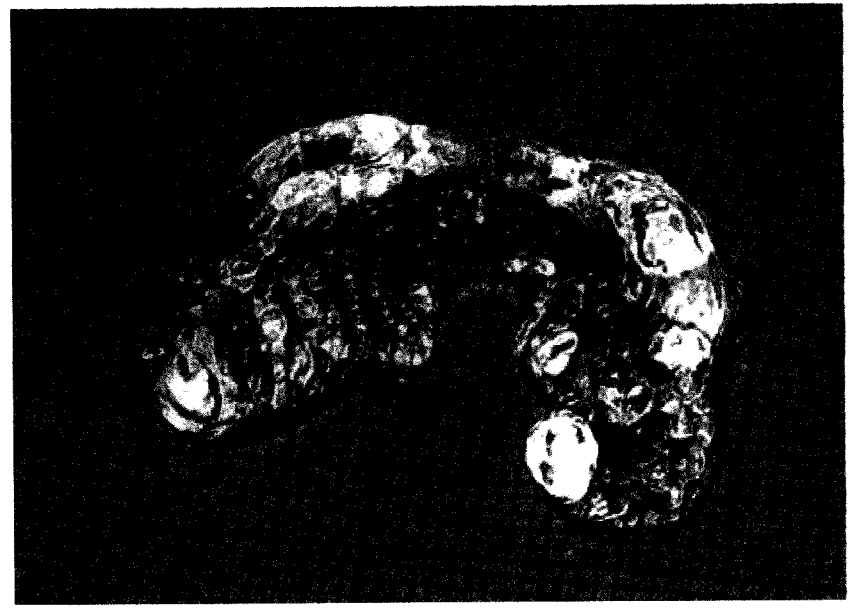
FIG. 27B is a photograph of a fabricated article produced by a fabrication system in accordance with the present invention.
Figure 27A:
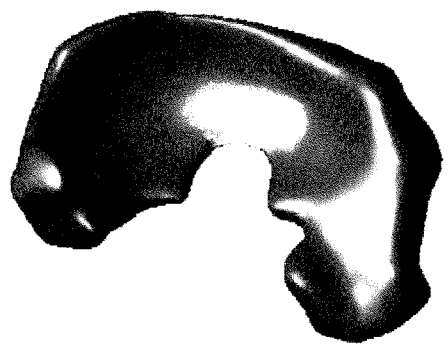
FIG. 27A is a CAD model image generated from a CT scan of a meniscus-shaped piece of cartilage used in fabricating the article shown in FIG. 27B.

The viability test verified short-term cellular survivability. In other words, the test determined whether the gel sustained life throughout the printing process, i.e., while being subjected to the shear forces induced by the deposition process. During viability testing, the printing process was simulated and then the percentage of living cells versus dead cells was measured before and after the simulated printing process. In order to count the percentage of living cells, two fluorescent chemical markers were used. Calcein acetoxymethyl (calcein AM) attaches to living cells and ethidium homodimer-1 (EthD-1) attaches to dead cells. Through the use of a fluorescent light source, a microscope, and the appropriate optical filters, the living and dead cells were identified (FIGS. 25A-B). The viability test did not have to be done under sterile conditions; the test was measuring short-term viability and infection would only have a long-term effect.

Process Sterility Test

The approach of using an autoclavable plastic bag as a printing envelope had to be tested to verify that no bacteria or fungi were allowed to infect the printed alginate gel. A sterile sample of alginate gel was prepared and placed in a sterile syringe. This syringe was then transported, with a sterilized syringe end-cap, to the printer and the full printing procedure was executed. After the printing, the sample was brought back to a sterile work hood where the envelope was opened and the sample removed. The gel sample was incubated for a period of eight days. After this incubation period, the sample was analyzed for presence of bacteria and fungi growth with the use of a chemical marker and fluorescence microscopy. It was determined that there was less than 1 bacterium per 0.9 µL after 8 days of incubation.

Direct CT Scan Printing Test

This research additionally demonstrated the ability to efficiently print a hydrogel implant directly from a CT scan. A CT scan of a meniscus cartilage was provided by the Cornell affiliated Hospital for Special Surgery (HSS) and then converted into an STL file. The STL file was then loaded into the CCSL software package and prepared for printing. The results of this direct CT Scan print are shown (FIGS. 26A-B and FIGS. 27A-B).

These results show the ability to successfully 3-D print viable, infection-free, living hydrogel implants of multiple materials with complex biological geometries. By printing with alginate hydrogels pre-seeded with gels, this technology serves as a versatile tissue engineering platform on which spatially heterogeneous implants of varied seeding densities, chemical concentrations, cell-types, etc., can be fabricated in arbitrary geometries. Additionally, the fabrication of implants generated directly from CT Scans brings this technology one step closer to its clinical form. This will allow patients to have, within hours, a complex, living, pre-seeded, multi-cell-type implant, such as an intervertebral disk, produced from prior CT Scans of their own healthy body parts.

Example 3

Direct Freeform Fabrication of Zinc-Air Batteries with Tailored Geometry and Performance In the following discussion, a cell is defined as a device that converts the chemical potential energy between its anode and cathode materials into electrical energy by means of redox reactions: reduction (electron gain) at the cathode, oxidation (electron loss) at the anode. A battery comprises of one or more connected cells. The essential functional components of a zinc-air ("Zn-air") cell are the anode terminal, cathode terminal, anode, separator, catalyst, electrolyte, and casing. The anode and cathode terminals are passive conductors that collect charge carriers and allow connection to external loads. The anode (zinc in this case) is one of the two key reactants in the cell. The other key reactant, oxygen, is derived directly from the atmosphere. The separator provides electrical insulation between the anode and cathode to prevent internal shorting, but must be permeable to electrolyte to allow ionic current flow. The catalyst accelerates the rate of chemical reaction at the electrolyte/atmosphere interface in a cell, improving power output. The electrolyte (aqueous potassium hydroxide ("aq. KOH") in this case), provides a medium for ionic transport within the cell and a source of ions. The casing provides an enclosure for the battery materials, permitting the battery to be handled without exposing the handler to the chemical reactants therein, and restricting the exposure of the reactants to the atmosphere, so that the evaporative loss of water from the electrolyte is reduced while still permitting the diffusion of atmospheric oxygen into the battery. The basic chemical reactions are:

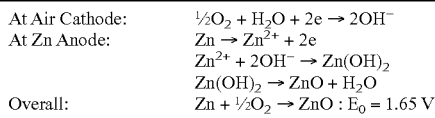

| At Air Cathode: | $\frac{1}{2}O_2 + H_2O + 2e \rightarrow 2OH^-$ |
|---|---|
| At Zn Anode: | $Zn \rightarrow Zn^{2+} + 2e$ |
| | $Zn^{2+} + 2OH^- \rightarrow Zn(OH)_2$ |
| | $Zn(OH)_2 \rightarrow ZnO + H_2O$ |
| Overall: | $Zn + \frac{1}{2}O_2 \rightarrow ZnO : E_0 = 1.65\ V$ |

Thus, the ideal output voltage of a zinc-air electrochemical cell is 1.65V. In practice, modes of energy dissipation within the cell limit open-circuit voltage to about 1.4V, and 1.2V under reasonable loading conditions.

In order to produce a Zn-air battery in accordance with the freeform fabrication system of the present invention, for each of the materials required to produce a battery, a formulation must be prepared which can be readily, automatically dispensed by at least one of the material deposition tools. This formulation process presents a significant challenge given the variety of materials involved. The availability within the system of multiple material deposition tools which make use of differing deposition processes provides greater freedom in the choice of materials and reduces the number of restrictions associated with selecting and formulating materials. The fact that the form of the finished battery is determined by the geometry data provided to the fabrication system permits a variety of single and multiple cell batteries, and a variety of battery shapes to be constructed without reformulation of materials or modification of method of fabrication.

A set of experiments concluded with the successful fabrication of a complete, functional Zn-air battery with the freeform fabrication system. The experiments (Malone et al., "Freeform Fabrication of 3D Zinc-air Batteries and Functional Electro-mechanical Assemblies," *Rapid Prototyping Journal* 10:58-69 (2004), which is hereby incorporated by reference in its entirety) employed two separate material deposition tools—a fusible-material deposition tool and a prototype version of a cartridge holding tool—with the freeform fabrication system to produce a complete, functional zinc-air battery.

The fusible-material deposition tool was used to deposit acrylonitrile-butadiene-styrene ("ABS") thermoplastic as the casing of the batteries. As this material has been used with this tool in a wide variety of other experiments, no special formulation was required.

The cartridge holding tool was used to deposit four different materials from four 10 mL disposable syringes, each syringe loaded with one of four materials. The first material was a methylcellulose gel filled with silver powder in order to render it electrically conductive. This material was used to form the anode terminal and cathode terminal. The second material was a slurry of zinc powder and aqueous potassium hydroxide at 8 Molar concentration, with a nonionic surfactant added to disperse the zinc powder and reduce friction in the material. This material was used to form the zinc anode. The third material was a slurry of ceramic particles in water with an adhesive binder. This material was used to form the electrically insulating separator. The fourth material was a slurry of manganese dioxide, carbon black, and aqueous potassium hydroxide. This material was used as the cathode catalyst.

Each of these materials required careful adjustment of the relative concentration of ingredients and, sometimes, the inclusion of additional ingredients in order to arrive at a formulation that can be dispensed from a syringe without clogging the syringe. All of the formulations had to be carefully tested and adjusted so that when deposited in the correct juxtapositions to each other, the aggregate behaved as a working electrochemical cell with reasonable power output. This is necessary since some of the formulation modifications which enhance the ability of the material to be dispensed may interfere with the desired electrochemical reactions.

Once acceptable formulations were arrived at for each of the four materials, a syringe needle was selected for that material which has a circular cross-section and an interior diameter as small as possible without being prone to becoming clogged by the material. The selection was made by mounting a syringe needle on a given syringe filled with one of the materials. The material was pushed through the needle manually using a standard disposable syringe plunger. If the entire contents of the syringe (approximately 10 mL) could be pushed through the needle without a clog forming, the needle was considered acceptable, and the test was repeated with a needle of smaller internal diameter. If a clog formed, a needle of larger internal diameter was tried. This process was iterated until the smallest needle was found that does not experience clogging.

Each material thus had an associated syringe needle which partially determined the geometry of the deposits of material that can be extruded from the syringe, and hence by the cartridge holding tool.

Other factors that affect the geometry of the deposits include the viscosity of the material, which determines whether it retains its shape or flows after having been deposited. It is generally desirable in freeform fabrication that materials have high viscosity so that they retain their shape upon being deposited, and can be stacked vertically without being contained or supported. Another factor is the height of the tip of the syringe needle above the surface onto which material will be deposited. This height should be roughly equivalent to the internal diameter of the syringe needle in order to achieve a roughly circular cross-section of deposited material. Yet another factor that affects the geometry of the deposits is the acceleration and speed with which the material is extruded from the syringe by the cartridge holding tool relative to the acceleration and speed with which the material deposition device moves the cartridge holding tool along a given path over the substrate. When these speeds are matched, the material will be deposited with roughly the cross-sectional dimensions of the syringe needle.

A calibration procedure was used to identify the accelerations, speeds, and distances which generate uniform, repeatable, and well-controlled deposits of material, as well as the relative position of the material deposition orifice of the tool to the position of the material deposition tool interface of the material deposition device. The calibration procedure was commenced for each material by entering the material name, the name of the material deposition tool used for depositing the material, and the initial estimated accelerations, speeds, and distances for the material into the materials/tools/substrates database of the system, mounting the cartridge holding tool onto the deposition device, loading a syringe of the particular material into a material cartridge and the cartridge into the cartridge holding tool, and commanding the system to produce a test pattern of the particular material by depositing it onto a substrate. The quality and geometry of the deposited test pattern was evaluated visually and with a caliper by the operator to determine whether the material deposits began, ended, maintained continuity, and maintained uniform cross-section as specified by the test pattern data. The parameters in the materials/tools/substrates database were adjusted and new test pattern deposits generated until the results were deemed satisfactory. The cross-sectional dimensions of the satisfactory material deposits were measured using the caliper. The height and width of the cross section of the deposits were entered into the materials/tools/substrates database with the other parameters. The parameters which generated the satisfactory results were used by the system for all subsequent deposition, including during the fabrication of a complete working battery.

Once the cross-section dimensions of material deposits and associated parameters were found for all of the materials, the battery to be fabricated was designed using SolidWorks three-dimensional mechanical computer-aided design ("MCAD") software. The battery designed was of a cylindrical shape. The design included an assembly of parts. A hollow cylindrical casing part contained stacked disk-shaped parts representing, from bottom to top, anode terminal, zinc anode, separator, cathode catalyst, and cathode terminal. The top-most part was a disk-shaped lid with holes intended to allow atmospheric oxygen to diffuse into the battery. Care was taken to ensure that the dimensions of each part of the battery assembly was larger than the cross-section dimensions of the material from which that part was to be fabricated. The data describing the geometry of the assembly (and all of the parts therein) was exported from the MCAD software as a set of STL format geometry data file.

The graphical user interface ("GUI") of the system software of the freeform fabrication system was used to import the STL files representing the geometry of the battery parts into the fabrication system. As the geometry of each part was imported, a shaded surface representation of the part was displayed to the user. The user used a feature of the GUI to assign a material from the materials/tools/substrates database to the part. The casing and casing lid were assigned the fusible-material deposition tool and the ABS thermoplastic material. All other parts were assigned the cartridge holding tool. The anode terminal and cathode terminal were assigned the methylcellulose material containing silver powder. The zinc anode part was assigned the zinc anode paste material. The separator part was assigned the separator ceramic slurry material. The cathode catalyst part was assigned the cathode catalyst slurry material.

Once all of the parts of the battery were imported into the system, the user commanded the software to generate a manufacturing plan. Using the names of the materials assigned to each of the parts, the manufacturing planning module of the software queried the materials/tools/substrates database for the cross-sectional dimensions of the materials. For each part, the planning module then uses the height of the cross-section of the material associated with that part to generate a family of parallel planes normal to the vertical (Z direction) axis of the system, spaced by the cross-section height of that material. The intersection of the part geometry with the family of planes is a family of closed curves (called "boundaries") which are uniformly spaced in height. At the height of each plane which intersected the part, the planning software generated a set of planar lines and curves (called "toolpaths") in the area enclosed by the boundaries, which resided in the horizontal (XY) plane at that height, and which are horizontally spaced from each other by the width of the cross-section of the material. The manufacturing planning software labeled the toolpaths with the name of the material deposition tool and the material associated with the part being processed.

This process was repeated for each part in the assembly which represented the battery to be fabricated, after which the manufacturing planning module sorted the toolpaths into a list according to several criteria, including the height of the toolpaths exported the set of labeled toolpaths (called the "manufacturing plan") to the operation control module of the system software.

The GUI informed the user that the manufacturing plan was completed. The user then commanded the system software to begin executing the manufacturing plan.

The operation control module performed a self-test routine for the material deposition device hardware. The operation control module then examined the first labeled toolpath in the manufacturing plan to identify the material deposition tool and material required. In this case, the first tool required was the fusible-material deposition tool, and the material was ABS thermoplastic. The operation control module determined that this tool was not yet mounted on the tool interface of the material deposition device. The GUI requested that the user attach this tool to the tool interface. The operation control module then queried the materials/tools/substrates database for the parameters associated with this tool and this material, which also included the location of the material deposition orifice of the tool relative to the location of the tool interface in the material deposition device coordinate system. The GUI then requested that the user command motion of the positioning system of the material deposition device until the orifice of the material deposition tool was adjacent to the desired point on the substrate at which the fabrication of the battery was desired to commence. The user employed the GUI to perform this action, and to inform the operation control module that this action was completed. The operation control module then recorded this position of the positioning system as the "build origin," and commenced to command the positioning system to trace out the first path in the manufacturing plan while simultaneously commanding the material deposition tool to deposit material onto the substrate, coordinating the commencement and termination of material deposition with the commencement and termination of positioning system motion along the path. Once this path was completed, subsequent paths in the manufacturing plan were examined by the operation control module. Several paths which described the bottom of the battery casing were executed in succession, resulting in a disk of ABS thermoplastic.

The next several paths in the manufacturing plan were labeled with the cartridge holding tool and the silver-filled methylcellulose material. The fabrication process was interrupted by the operation control module, which commanded the positioning system to move to a corner of its range of motion while employing the GUI to request that the user remove the fusible material deposition tool from the tool interface, and replace it with the cartridge holding tool and ensure that a cartridge containing a syringe filled with the silver-filled methylcellulose material was mounted in the cartridge socket of the tool. The user performed these actions and signaled their completion using the GUI. The operation control module then resumed the fabrication process by querying the materials/tools/substrates database for the orifice coordinates for this tool and material, and adjusting the positioning system coordinate system to reflect the difference in the orifice coordinates between the two tools. The operation control module commanded the positioning system to position the orifice of the tool at the coordinates of the starting point of the next toolpath, and commanded the tool and deposition device to deposit material along the path as before, only using the parameters from the materials/tools/substrates database for this tool and this material.

This same set of operations was continued by the system for each path in the manufacturing plan, requesting that the user change the tool and/or material cartridge according to the labels of the paths.

After the deposition of the anode terminal, fabrication of the hollow cylindrical wall of the casing with the fusible material deposition tool and ABS material was alternated with fabrication of the other parts of the battery using the cartridge holding tool and the appropriate material cartridges, progressively building upward in height. The zinc anode was deposited atop the anode terminal. Then the separator, cathode catalyst and cathode conductor were deposited. Finally the fusible material deposition tool and ABS material were used to deposit the casing lid, which completed the fabrication of the functional zinc-air battery.

The finished battery measured approximately 50 mm in diameter by 10 mm high, produced more than 1.4 V open-circuit, and was able to produce enough power (approximately 30 mW) to rotate a small electric motor for a few seconds.

This example demonstrates the ability of the freeform fabrication system to fabricate complete functional articles which comprise multiple active materials while employing a plurality of material deposition tools which operate by different material deposition mechanisms. In addition, the system fabricates these articles using a labeled geometric description of the desired article and its subcomponents, and there are very few restrictions on the geometry of the article. This description can be generated in a manner of minutes, permitting a continuum of article designs to be produced by the same system with no specialization or modification of the system.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of fabricating a living three-dimensional structure, said method comprising:
   providing a data set representing a living three-dimensional structure to be fabricated;
   providing a printable composition comprising a hydrogel seeded with cells, wherein the hydrogel comprises collagen; and
   printing the printable composition onto a substrate in layers in a pattern in accordance with the data set suitable to fabricate the living three-dimensional structure without the need to provide a negative template;
   wherein the printable composition is capable of bonding between printed layers; and
   wherein 94±5% of the cells in the fabricated living three-dimensional structure are viable.

2. The method according to claim 1, wherein the hydrogel further comprises chitosan, fibrin, hyaluronic acid, carrageenan, polyethylene oxide, polypropylene oxide, polyethylene oxide-co-polypropylene oxide, hydroxypropyl methyl cellulose, polypropylene fumarate-co-ethylene glycol), poly (ethylene glycol)-co-poly(lactic acid), poly(vinyl alcohol), KDL12 oligopeptides, or poly(n-isopropyl acrylamide).

3. The method according to claim 1, wherein the hydrogel further comprises a cross-linking compound.

4. The method according to claim 1, wherein the cells are of a single cell type.

5. The method according to claim 4, wherein the cells are chondrocytes.

6. The method according to claim 1, wherein the cells are of more than one cell type.

7. The method according to claim 1, wherein said printing is carried out under sterile conditions.

8. The method according to claim 7, wherein said printing is carried out in a hermetically sealed envelope.

9. The method according to claim 1, wherein the data set comprises geometry and cell distribution data of the structure to be fabricated, the method further comprising:
   programming a system controller with instructions effective to cause said printing to produce a living three-dimensional structure with a desired geometry and cell distribution.

10. The method according to claim 9, wherein the geometry is free-form.

11. The method according to claim 9, wherein the geometry is an anatomic shape.

12. The method according to claim 11, wherein the anatomic shape is patient-specific.

13. The method according to claim 1, wherein the data set is generated by a computerized scan of a tissue/organ.

14. The method according to claim 13, wherein the computerized scan is achieved by computerized tomography and magnetic resonance imaging.

15. The method according to claim 1 further comprising: incubating the living three-dimensional structure under conditions effective to grow the cells.

16. The method according to claim 1, wherein the composition is printed from a syringe.

17. The method according to claim 1, wherein the composition is printed from a deposition tool with an accuracy and repeatability of ±25 μm.

18. The method according to claim 1, wherein said printing is carried out at a maximum applied pressure of 1592 kPa.

19. The method according to claim 1, wherein said printing is carried out at a maximum volumetric flow of 10.5 mL/s.

* * * * *